United States Patent
Centis et al.

(10) Patent No.: US 12,171,900 B2
(45) Date of Patent: Dec. 24, 2024

(54) MULTI-DIMENSIONAL HEMOSTATIC PRODUCT AND METHOD FOR PRODUCING THE SAME

(71) Applicant: BIOM'UP FRANCE SAS, Saint-Priest (FR)

(72) Inventors: Valérie Centis, Lyons (FR); Emmanuelle Monchaux, Lyons (FR)

(73) Assignee: DILON TECHNOLOGIES INC., Newport News, VA (US)

( * ) Notice: Subject to any disclaimer, the term of this patent is extended or adjusted under 35 U.S.C. 154(b) by 1168 days.

(21) Appl. No.: 16/970,094

(22) PCT Filed: Feb. 15, 2019

(86) PCT No.: PCT/EP2019/053896
§ 371 (c)(1),
(2) Date: Aug. 14, 2020

(87) PCT Pub. No.: WO2019/158734
PCT Pub. Date: Aug. 22, 2019

(65) Prior Publication Data
US 2021/0162095 A1    Jun. 3, 2021

(30) Foreign Application Priority Data
Feb. 15, 2018   (EP) .................................... 18305154

(51) Int. Cl.
*A61L 24/10*   (2006.01)
*B33Y 10/00*   (2015.01)
(Continued)

(52) U.S. Cl.
CPC ............. *A61L 24/102* (2013.01); *B33Y 10/00* (2014.12); *B33Y 70/00* (2014.12); *B33Y 80/00* (2014.12);
(Continued)

(58) Field of Classification Search
CPC ............. A61L 24/102; A61L 2300/232; A61L 2400/04; A61L 2400/06; B33Y 80/00
See application file for complete search history.

(56) References Cited

U.S. PATENT DOCUMENTS

| | | |
|---|---|---|
| 4,427,651 A | 1/1984 | Stroetmann |
| 4,891,359 A | 1/1990 | Saferstein et al. |
| (Continued) | | |

FOREIGN PATENT DOCUMENTS

| | | |
|---|---|---|
| CA | 2485268 A1 | 11/2003 |
| CN | 1554448 A | 12/2004 |
| (Continued) | | |

OTHER PUBLICATIONS

"Rich's Vascular Trauma", 3rd edition, edited by Todd E. Rasmussen and Nigel R. M. Tai, 2016, Chapter 16, "Damage Control: Prehospital Care of the Patient With Vascular Injury," by L. H. Blackbourne and F. K. Butler (pp. 188-189 included). (Year: 2016).*
(Continued)

*Primary Examiner* — Vu A Nguyen
(74) *Attorney, Agent, or Firm* — Birch, Stewart, Kolasch & Birch, LLP

(57) ABSTRACT

The invention relates to a printed hemostatic product having at least three-dimensions and being made of a stack of layers deposited on one another from a first external layer up to a second external layer, wherein adjacent layers of the stack of layers are joined together, and wherein at least one layer of the stack of layers has at least one portion made from an hemostatic flowable with a composition comprising: non-cross-linked collagen of the fibrillar type comprising a content of fibrous collagen and/or fibrillar collagen of at least 70% by weight relative to the total weight of the collagen; and—at least one monosaccharide. The invention also relates to a method for forming such an hemostatic product with a three-dimensional additive printer, and the
(Continued)

use of an hemostatic flowable as a printing ink in such a three-dimensional additive printer.

20 Claims, 2 Drawing Sheets

(51) Int. Cl.
| | |
|---|---|
| B33Y 70/00 | (2020.01) |
| B33Y 80/00 | (2015.01) |
| C09D 11/033 | (2014.01) |
| C09D 11/04 | (2006.01) |
| C09D 11/14 | (2006.01) |

(52) U.S. Cl.
CPC ............ *C09D 11/033* (2013.01); *C09D 11/04* (2013.01); *C09D 11/14* (2013.01); *A61L 2300/232* (2013.01); *A61L 2400/04* (2013.01); *A61L 2400/06* (2013.01)

(56) References Cited

U.S. PATENT DOCUMENTS

| | | | |
|---|---|---|---|
| 4,942,153 A | | 7/1990 | Fernandez |
| 6,280,727 B1 | | 8/2001 | Prior et al. |
| 9,283,187 B2 | * | 3/2016 | Gagnieu ............ A61K 38/4833 |
| 9,662,374 B2 | | 5/2017 | Gagnieu et al. |
| 10,046,034 B2 | | 8/2018 | Gagnieu et al. |
| 2005/0147679 A1 | | 7/2005 | Petito et al. |
| 2005/0208114 A1 | | 9/2005 | Petito et al. |
| 2006/0019868 A1 | | 1/2006 | Pendharkar |
| 2006/0073207 A1 | | 4/2006 | Masters et al. |
| 2006/0159731 A1 | * | 7/2006 | Shoshan ................ A61K 38/39 |
| | | | 424/443 |
| 2007/0009578 A1 | | 1/2007 | Moller et al. |
| 2007/0140984 A1 | | 6/2007 | Kusano et al. |
| 2008/0021374 A1 | | 1/2008 | Kawata |
| 2009/0082849 A1 | | 3/2009 | Dowling et al. |
| 2009/0192429 A1 | | 7/2009 | Daniels et al. |
| 2012/0040119 A1 | | 2/2012 | Gagnieu et al. |
| 2014/0018729 A1 | | 1/2014 | Foster et al. |
| 2014/0081192 A1 | | 3/2014 | Wenske et al. |
| 2019/0168444 A1 | | 6/2019 | Katsumura et al. |

FOREIGN PATENT DOCUMENTS

| | | |
|---|---|---|
| CN | 1709507 A | 12/2005 |
| CN | 1921896 A | 2/2007 |
| CN | 101001649 A | 7/2007 |
| CN | 101272790 A | 9/2008 |
| CN | 101757614 A | 6/2010 |
| CN | 101837143 A | 9/2010 |
| CN | 101883545 A | 11/2010 |
| DE | 19620676 A1 | 12/1996 |
| EP | 0145970 A2 | 6/1985 |
| EP | 1580229 A1 | 9/2005 |
| EP | 1905443 A1 | 4/2008 |
| FR | 2944706 A1 | 10/2010 |
| JP | 2003-62057 A | 3/2003 |
| JP | 2014-36882 A | 2/2014 |
| JP | 2014-508615 A | 4/2014 |
| JP | 2014-512403 A | 5/2014 |
| JP | 2014-514942 A | 6/2014 |
| JP | 2014-518250 A | 7/2014 |
| JP | 2015-525647 A | 9/2015 |
| WO | WO 93/21857 A1 | 11/1993 |
| WO | WO 95/03786 A2 | 2/1995 |
| WO | WO 98/57678 A2 | 12/1998 |
| WO | WO 00/10540 A1 | 3/2000 |
| WO | WO 01/97871 A2 | 12/2001 |
| WO | WO 01/97873 A2 | 12/2001 |
| WO | WO 02/098223 A1 | 12/2002 |
| WO | WO 03/026709 A1 | 4/2003 |
| WO | WO 03/094983 A1 | 11/2003 |
| WO | WO 2005/092968 A1 | 10/2005 |
| WO | WO 2005/115252 A1 | 12/2005 |
| WO | WO 2005/072700 A2 | 8/2006 |
| WO | WO 2009/088926 A1 | 7/2009 |
| WO | WO 2009/109963 A1 | 9/2009 |
| WO | WO 2010/125086 A1 | 11/2010 |
| WO | WO 2012/136701 A1 | 10/2012 |
| WO | WO 2012/146655 A1 | 11/2012 |
| WO | WO 2013/004838 A1 | 1/2013 |
| WO | WO 2014/024048 A1 | 2/2014 |
| WO | WO 2017/011050 A2 | 1/2017 |
| WO | WO 2017/213170 A1 | 12/2017 |

OTHER PUBLICATIONS

Avery et al., "The Effects of the Maillard Reaction on the Physical Properties and Cell Interactions of Collagen", Pathologie Biologie, vol. 54, 2006, pp. 387-395, XP024926173.

Buehler, "Nature Designs Tough Collagen: Explaining the Nanostructure of Collagen Fibrils," PNAS, vol. 103, No. 33, Aug. 15, 2006, pp. 12285-12290.

Caruso et al., "Changes in Mechanical Properties and Cellularity during Long-term Culture of Collagen Fiber ACL Reconstruction Scaffolds," Wiley Interscience, vol. 74, No. 4, Jun. 15, 2005 (Published online May 6, 2005), pp. 388-397.

Chinese Office Action dated Jan. 2, 2019 for Chinese Application No. 201610756407.6.

European Search Report, dated Aug. 5, 2011, for European Application No. 11305492.8.

Extended European Search Report, dated Aug. 14, 2018, for European Application No. 18305154.9.

Extended European Search Report, dated Feb. 16, 2017, for European Application No. 16184119.2.

Gladman et al., "Biomimetic 40 Printing," Nature Materials, vol. 15, Published online Jan. 25, 2016, 27 pages.

Gross et al., "Extraction of Collagen from Connective Tissue by Neutral Salt Solutions," Proceedings of the National Academy of Sciences, vol. 41, No. 1, Jan. 15, 1955, pp. 1-7 (6 pages total).

Hattori et al., "Alkali-Treated Collagen Retained the Triple Helical Conformation and the Ligand Activity for the Cell Adhesion via $\alpha^2\beta 1$ Integrin," J Biochem., vol. 125, No. 4, 1999, pp. 678-884.

International Search Report and Written Opinion of the International Searching Authority, dated Jul. 17, 2012, for International Application No. PCT/EP2012/057647.

International Search Report and Written Opinion of the International Searching Authority, dated May 13, 2019, for International Application No. PCT/EP2019/053896.

Karagiannis et al., "Experience from the Use of Absorbable Type I Collagen as Haemostatic Agent in Obstetric and Gynecological Operations," Hippokratia 2006, vol. 10, No. 2, 2006, pp. 182-184.

Kirchmajer et al. "An Overview of the Suitability of Hydrogel Forming Polymers for Extrusion-based 3D-printing," Journal of Materials Chemistry B, Apr. 29, 2015, 14 pages.

Ohan et al., "Glucose Stabilizes Collagen Steralized with Gamma Irradiation," J Biomed Mater Res A, vol. 67, No. 4. Dec. 15, 2003, pp. 1188-1195.

Ozbolat et al., "Current Advances and Future Perspectives in Extrusion-based Bioprinting." Biomaterials, vol. 76, 2016 (Available online Oct. 31, 2015), pp. 321-343.

Retsch Inc, Centrifugal Mill Brochure, with evidence of attachment at p. 23 to show the product was used before Nov 1. 2006, https://www.pcimag.com/articles/87099-grinding-of-powder-coatings, downloaded from Internet on Jun. 6, 2015, 28 p. .

Shoulders et al., "Collagen Structure and Stability," Annu. Rev. Biochem, vol. 78, 2009 (First published online Apr. 3, 2009), pp. 929-958.

Singh et al., "Hemostatic Comparison of a Polysaccharide Powder and a Gelatin Powder," Journal of Investigative Surgery, vol. 27, No. 4. 2018 (Published online Feb. 8, 2018), pp. 1-9 (10 pages total).

Van Der Rest et al., "Collagen Family of Proteins," The FASEB Journal, vol. 5, Oct. 1991, pp. 2814-2823.

(56) References Cited

OTHER PUBLICATIONS

Written Opinion of the International Searching Authority and International Search Report, dated Oct. 26, 2017, for International Application No. PCT/EP2017/070428.

* cited by examiner

MULTI-DIMENSIONAL HEMOSTATIC PRODUCT AND METHOD FOR PRODUCING THE SAME

FIELD OF THE INVENTION

The present invention relates to the field of hemostatic compositions, in particular to printed hemostatic products, for example a three-dimensional (3D) hemostatic product, and to a method for manufacturing such a three-dimensional hemostatic product.

TECHNICAL BACKGROUND

Wounds, whether external or internal, traumatic or surgical, frequently lead to bleeding. Such bleeding can be more or less significant. Bleeding is prevented and stopped via a set of physiological phenomena called "hemostasis". Hemostasis helps repair the vascular breach and, generally, ensures the maintenance of vessel and tissue integrity.

When a blood vessel is injured, a natural mechanism comprising various stages is triggered to stem the flow of blood. First, vasoconstriction, which slows the bleeding, lasts for 15 to 60 seconds and induces a complex cascade of reactions. A fibrous mesh composed of fibrin forms around the platelet plug: the final thrombus is formed and is protected from premature dissolution by factor XIII, which stabilizes fibrin. Finally, the fibrin mesh draws tighter (retraction) and the edges of the wound come together: the wound shrinks. Within the stable, cross-linked fibrin, fibroblasts can then grow and organize into a conjunctive matrix within the thrombus and finally close the wound.

No solid fibrin is present in circulating blood; if it were it would immediately obstruct vital vessels. However, fibrin's precursor, fibrinogen, is present. Under the action of thrombin, whose synthesis is activated by coagulation factors, fibrinogen is transformed into insoluble fibrin.

Lastly, several days or weeks after successful healing of the wound, the fibrin cluster is destroyed during fibrinolysis.

In spite of this biochemical phenomenon, it is often necessary, in particular in the case of wounds that are too large or in the case of diffuse bleeding, to "artificially" carry out hemostasis.

There are "mechanical" solutions to help obtain hemostasis, such as pressure, ligature and electrocoagulation, which are used as first-line treatments. However, these solutions have little or no effectiveness in a certain number of cases, such as oozing capillary hemorrhages, hemorrhages of hypervascularized organs such as the spleen or liver, hemorrhages leading to diffuse bleeding, for example bones, and/or in neurosurgery.

"Chemical" solutions, in particular implemented in certain current hemostatic products, also exist. The components of said chemical solutions are in general either of the "absorbent" or "active" type.

Absorbent hemostatic products, notably comprising polysaccharides such as regenerated oxidized cellulose or alginates, work mainly by mechanical action and simple absorption. They frequently present a problem of excessive swelling. If said swelling leads to rapid absorption of liquid, in particular blood, it can also lead to undesirable pressure when used in a "closed" environment, for example in contact with the dura mater or in urology.

In addition, certain products, notably those comprising plant polysaccharides such as cellulose or alginates, can further cause inflammatory reactions during their resorption and/or can lead to degradation products not recognized by the host. The consequence of this is that it is desirable to remove such products so that they do not remain in the body and thus do not produce these adverse effects.

Active hemostatic products, such as products containing thrombin or fibrin, are often blood-derived products. Such products involve risks of allergies and disease transmission, in particular in the case where the disease vector would not be inactivated by classically applied treatments. In addition, said downstream treatments are generally complex and/or costly. Lastly, in general they can require preparation before use, which can be a constraint, indeed a nuisance, in terms of an emergency.

Moreover, products containing both fibrin and thrombin base their mode of action on the interaction between the two blood-derived products comprising the product. The reaction can occasionally take place without interaction with the blood, in which case the products are said to float. In other words, the product is pushed away by the blood which continues to flow, possibly causing the product to become diluted or to coagulate and form a gel on top of the blood, a situation in which the flow of blood is not blocked. Hemostasis can thus not be achieved.

An hemostatic powder, its method of production and method of use, have been disclosed in the international application published under the reference WO 2012/146655 on 1 Nov. 2012, the content of which is entirely incorporated by reference in the present application.

Such hemostatic powder has a satisfactory absorption capacity, good hemostatic capacity, almost no adverse effects, good capacity to anchor on the edge of the wound and satisfactory penetration in the blood flow where it is used and/or limited swelling.

In addition to these good hemostatic properties, such hemostatic powder presents the advantage of having a very good flowability that enables it to be sprayed on the bleeding region. It can be administered in most surgical procedures, such as laparotomies, laparoscopies, coelioscopies, and robotic surgical techniques.

The hemostatic powder can be directly applicable on the bleeding region without specific preparation by the surgeon which is another advantage.

It might sometimes be necessary to use specific powder dispensers to ease the application of the hemostatic powder on a very specific bleeding region.

The aim of the present invention is to propose an hemostatic product that is simple to use, and especially does not need a complex preparation process, which can further be easily applied on a specific area to cover the whole bleeding region of interest.

Another aim of the present invention is to propose an hemostatic product that has a good hemostasis efficacy, and an enhanced efficacy compared to existing hemostatic products.

Still another aim of the present invention is to propose a hemostatic product which can be adapted to a very specific need of a patient, and that can be easily manufactured.

A further aim of the present invention is to propose a hemostatic product which can be use in areas of multiple bleeding and/or where the bleeding area has a complex form.

It is also an aim of the present invention to propose a manufacturing method of a three-dimensional hemostatic product which is easy to carry out and that enables forming complex three-dimensional hemostatic product.

SUMMARY OF THE INVENTION

To this end, there is proposed a multi-dimensional hemostatic product, a method of manufacturing thereof, and the use of an hemostatic flowable as defined in the appended claims.

More precisely, there is proposed a three-dimensional hemostatic product made of a stack of layers deposited on one another from a first external layer up to a second external layer, wherein adjacent layers are joined together, characterized in that at least one of the first and second external layers of the stack of layers is made from an hemostatic flowable mixture of:
- collagen of the fibrillar type, such collagen being preferably non-cross-linked, comprising a content of fibrous collagen and/or fibrillar collagen of at least 70% by weight relative to the total weight of the collagen;
- at least one monosaccharide; and
- at least one glycosaminoglycan.

Preferable but non-limiting aspects of such a three-dimensional hemostatic product, taken alone or in combination, are the following:
- the first and second external layers of the stack of layers have the same composition.
- each layer of the stack of layers has a periphery made from a flowable mixture identical to the flowable mixture of the at least one of the first and second external layers.
- all layers of the stack of layers have the same composition.

There is also proposed the use of an hemostatic flowable as a printing ink in a three-dimensional printer, wherein the hemostatic flowable is made of a hemostatic powder mixed with a saline solution, wherein the hemostatic powder has a composition comprising:
- non-cross-linked collagen of the fibrillar type comprising a content of fibrous collagen and/or fibrillar collagen of at least 70% by weight relative to the total weight of the collagen;
- at least one monosaccharide; and
- at least one glycosaminoglycan.

There is further proposed a method of manufacturing a three-dimensional hemostatic product with a three-dimensional additive printer, comprising the following steps:
- providing a three-dimensional model to the three-dimensional additive printer, said three-dimensional model corresponding to the shape of the three-dimensional hemostatic product to be manufactured, and processing said three-dimensional model to define a printing pattern with a plurality of layers designed to be stacked on one another so as to form a stack of layers corresponding to the three-dimensional model;
- providing a hemostatic flowable to the three-dimensional additive printer for use as a printing ink, wherein said flowable is made of an hemostatic powder mixed with a saline solution, wherein the hemostatic powder has a composition comprising:
  - non-cross-linked collagen of the fibrillar type comprising a content of fibrous collagen and/or fibrillar collagen of at least 70% by weight relative to the total weight of the collagen;
  - at least one monosaccharide; and
  - at least one glycosaminoglycan;
- depositing the hemostatic flowable with the three-dimensional additive printer to form at least one of the external layers of the stack of layers.

For such method of manufacturing a three-dimensional hemostatic product, the hemostatic flowable is preferably used to form all the layers of the stack of layers in order to obtain the three-dimensional hemostatic product (10).

Preferable but non-limiting aspects of the hemostatic flowable described above, taken alone or in combination, are the following:

- in the composition of the hemostatic powder:
  - the collagen is in an amount ranging from 80% to 90% by weight relative to the total weight of the composition of the hemostatic powder;
  - the at least one monosaccharide is in an amount ranging from 1% to 12.5% by weight relative to the total weight of the composition of the hemostatic powder; and
  - the at least one glycosaminoglycan is in an amount ranging from 2% to 25% by weight relative to the total weight of the composition of the hemostatic powder.
- in the composition of the hemostatic powder:
  - the collagen is in an amount ranging from 80% to 90% by weight relative to the total weight of the composition of the hemostatic powder;
  - the at least one monosaccharide is in an amount ranging from 2.5% to 7.5% by weight relative to the total weight of the composition of the hemostatic powder; and
  - the at least one glycosaminoglycan is in an amount ranging from 5% to 12.5% by weight relative to the total weight of the composition of the hemostatic powder.
- in the composition of the hemostatic powder:
  - the collagen is in an amount ranging from 84% to 88% by weight relative to the total weight of the composition of the hemostatic powder;
  - the at least one monosaccharide is in an amount ranging from 4% to 6% by weight relative to the total weight of the composition of the hemostatic powder; and
  - the at least one glycosaminoglycan is in an amount ranging from 8% to 10% by weight relative to the total weight of the composition of the hemostatic powder.
- in the composition of the hemostatic powder, the at least one monosaccharide is glucose and the at least one glycosaminoglycan is chondroitin sulfate.
- in the composition of the hemostatic powder, the at least one glycosaminoglycan is chosen among chondroitin sulfate, dermatan sulfate, hyaluronic acid and mixtures thereof.
- the composition of the hemostatic powder further comprises at least one coagulation factor in an amount lower than 0.1% by weight relative to the total weight of the composition of the hemostatic powder.
- the coagulation factor is thrombin.
- the saline solution comprises—or consists of—distilled water and sodium chloride, wherein the sodium chloride is in an amount ranging from 0.5% to 1.5% by weight relative to the total weight of the saline solution, most preferably in an amount of 0.9% by weight relative to the total weight of the saline solution.
- the mass of the saline solution is between 2 to 10 times of the mass of the hemostatic powder, and preferably between 4 to 5 times of the mass of the hemostatic powder.
- the hemostatic flowable is made by mixing between 1 g and 2 g of the hemostatic powder with between 4 mL and 10 mL of saline solution, preferably between 5 mL and 10 mL of saline solution.
- the hemostatic flowable is made by mixing 1.65 g of hemostatic powder mixed with 7 mL of pure saline solution, or any other similar ratio.

There is also proposed a printed hemostatic product having at least three-dimensions and being made of a stack of layers deposited on one another from a first external layer up to a second external layer, wherein adjacent layers of the stack of layers are joined together, and wherein at least one layer of the stack of layers has at least one portion made from an hemostatic flowable with a composition comprising:

non-cross-linked collagen of the fibrillar type comprising a content of fibrous collagen and/or fibrillar collagen of at least 70% by weight relative to the total weight of the collagen; and at least one monosaccharide.

Preferable but non-limiting aspects of such printed hemostatic product, taken alone or in combination, are the following:

the at least one layer of the stack of layers has several portions made from hemostatic flowables with different compositions.

the at least one layer of the stack of layers is fully made from the same hemostatic flowable.

all layers of the stack of layers have the same composition.

the printed hemostatic product comprises a plurality of adjacent layers, each layer of the plurality of adjacent layers having at least one portion made from the hemostatic flowable.

at least one of the first and second external layers of the stack of layers has a portion made from the hemostatic flowable.

the at least one of the first and second external layers is fully made from the same hemostatic flowable.

the first and second external layers of the stack of layers have the same composition.

each layer of the stack of layers has a peripheral portion made from a flowable mixture identical to the flowable mixture of the at least one of the first and second external layers.

at least one layer of the stack of layers comprises a portion made from an hemostatic flowable having swelling properties different from the swelling properties of the other layers of the stack of layers.

the composition of the hemostatic flowable comprises a collagen content ranging from 70% to 99% by weight relative to the total weight of the composition, preferably ranging from 75% to 96% by weight, and even more preferably ranging from 80% to 90% by weight.

the composition of the hemostatic flowable comprises a monosaccharide content ranging from 1% to 12.5% by weight relative to the total weight of the composition, preferably ranging from 2% to 8% by weight, more preferably ranging from 2.5% to 7.5% by weight, and even more preferably ranging from 4% to 6% by weight.

the composition of the hemostatic flowable comprises at least one glycosaminoglycan.

the glycosaminoglycan is in a content ranging from 1% to 30% by weight relative to the total weight of the composition, preferably ranging from 2% to 25% by weight, preferably ranging from 4% to 15% by weight, more preferably ranging from 5% to 12.5% by weight, and even more preferably ranging from 8% to 10% by weight.

the glycosaminoglycan is chosen among chondroitin sulfate, dermatan sulfate, hyaluronic acid and mixtures thereof.

the composition of the hemostatic flowable comprises at least one coagulation factor, in particular thrombin.

the coagulation factor is in an amount ranging from 0.01 IU/mg to 20 IU/mg of the composition, preferably ranging from 0.05 IU/mg to 10 IU/mg of the composition, more preferably ranging from 0.1 IU/mg to 5 IU/mg of the composition, and even more preferably ranging from 0.2 IU/mg to 2 IU/mg of the composition.

the hemostatic flowable is made with an hemostatic powder having a composition comprising:

a collagen of the fibrillar type comprising a content of fibrous collagen and/or fibrillar collagen of at least 70% by weight relative to the total weight of the collagen, said collagen being in an amount ranging from 75% to 96% by weight relative to the total weight of the composition of the hemostatic powder, preferably ranging from 80% to 90% by weight;

a at least one monosaccharide in an amount ranging from 1% to 12.5% by weight relative to the total weight of the composition of the hemostatic powder, preferably an amount ranging from 2.5% to 7.5% by weight, and more preferably an amount ranging from 4% to 6% by weight.

the hemostatic powder further comprises at least one glycosaminoglycan in an amount ranging from 1% to 30% by weight relative to the total weight of the composition of the hemostatic powder, preferably ranging from 2% to 25% by weight, preferably an amount ranging from 4% to 15% by weight, more preferably an amount ranging from 5% to 12.5% by weight, and even more preferably an amount ranging from 8% to 10% by weight.

the hemostatic powder further comprises at least one coagulation factor in an amount lower than 0.5% by weight relative to the total weight of the composition of the hemostatic powder, preferably in an amount lower than 0.1% by weight.

There is further proposed the use of an hemostatic flowable as a printing ink in a three-dimensional printer, wherein the hemostatic flowable is made of a hemostatic powder mixed with a saline solution, wherein the hemostatic powder has a composition comprising:

non-cross-linked collagen of the fibrillar type comprising a content of fibrous collagen and/or fibrillar collagen of at least 70% by weight relative to the total weight of the collagen;

at least one monosaccharide.

Preferable but non-limiting aspects of such use of an hemostatic flowable as a printing ink, taken alone or in combination, are the following:

the composition of the hemostatic powder forming the hemostatic flowable comprises a collagen content ranging from 70% to 99% by weight relative to the total weight of the composition, preferably ranging from 75% to 96% by weight, and even more preferably ranging from 80% to 90% by weight.

the composition of the hemostatic powder forming the hemostatic flowable comprises a monosaccharide content ranging from 1% to 12.5% by weight relative to the total weight of the composition, preferably ranging from 2% to 8% by weight, more preferably ranging from 2.5% to 7.5% by weight, and even more preferably ranging from 4% to 6% by weight.

the composition of the hemostatic powder forming the hemostatic flowable comprises at least one glycosaminoglycan.

the glycosaminoglycan is in a content ranging from 1% to 30% by weight relative to the total weight of the composition, preferably ranging from 2% to 25% by weight, preferably ranging from 4% to 15% by weight, more preferably ranging from 5% to 12.5% by weight, and even more preferably ranging from 8% to 10% by weight.

the glycosaminoglycan is chosen among chondroitin sulfate, dermatan sulfate, hyaluronic acid and mixtures thereof.

the composition of the hemostatic powder forming the hemostatic flowable comprises at least one coagulation factor, in particular thrombin.

the coagulation factor is in an amount ranging from 0.01 IU/mg to 20 IU/mg of the composition, preferably ranging from 0.05 IU/mg to 10 IU/mg of the composition, more preferably ranging from 0.1 IU/mg to 5 IU/mg of the composition, and even more preferably ranging from 0.2 IU/mg to 2 IU/mg of the composition.

the saline solution comprises at least one coagulation factor, in particular thrombin.

the coagulation factor is in an amount ranging from 10 IU/mL to 5000 IU/mL of the saline solution, preferably ranging from 25 IU/mL to 2500 IU/mL of the saline solution, more preferably ranging from 50 IU/mL to 1000 IU/mL of the saline solution, and even more preferably ranging from 100 IU/mL to 500 IU/mL of the saline solution.

the composition of the hemostatic powder forming the hemostatic flowable comprises:
  collagen of the fibrillar type comprising a content of fibrous collagen and/or fibrillar collagen of at least 70% by weight relative to the total weight of the collagen, said collagen being in an amount ranging from 75% to 96% by weight relative to the total weight of the composition of the hemostatic powder, preferably ranging from 80% to 90% by weight;
  least one monosaccharide in an amount ranging from 1% to 12.5% by weight relative to the total weight of the composition of the hemostatic powder, preferably an amount ranging from 2.5% to 7.5% by weight, and more preferably an amount ranging from 4% to 6% by weight.

the composition of the hemostatic powder forming the hemostatic flowable further comprises at least one glycosaminoglycan in an amount ranging from 1% to 30% by weight relative to the total weight of the composition of the hemostatic powder, preferably ranging from 2% to 25% by weight, preferably an amount ranging from 4% to 15% by weight, more preferably an amount ranging from 5% to 12.5% by weight, and even more preferably an amount ranging from 8% to 10% by weight.

the hemostatic powder forming the hemostatic flowable further comprises at least one coagulation factor in an amount lower than 0.5% by weight relative to the total weight of the composition of the hemostatic powder, preferably in an amount lower than 0.1% by weight.

the mass of the saline solution used to form the hemostatic flowable is between 2 to 10 times of the mass of the hemostatic powder, and preferably between 4 to 5 times of the mass of the hemostatic powder.

the hemostatic powder forming the hemostatic flowable comprises at least 80% by weight of particles whose size is between 20 µm and 300 µm.

the hemostatic powder forming the hemostatic flowable comprises at least 90% by weight of particles whose size is lower than 350 µm.

There is finally proposed a method of manufacturing an hemostatic product having at least three dimensions with a three-dimensional additive printer, comprising the following steps:
  a) providing a three-dimensional model to the three-dimensional additive printer, said three-dimensional model corresponding to the structure of the hemostatic product to be manufactured, and processing said three-dimensional model to define a printing pattern with a plurality of layers designed to be stacked on one another so as to form a stack of layers corresponding to the three-dimensional model;
  b) providing at least one hemostatic flowable to the three-dimensional additive printer for use as a printing ink, wherein said flowable is made of an hemostatic powder mixed with a saline solution, wherein the hemostatic powder has a composition comprising:
    non-cross-linked collagen of the fibrillar type comprising a content of fibrous collagen and/or fibrillar collagen of at least 70% by weight relative to the total weight of the collagen; and
    at least one monosaccharide;
  c) printing the hemostatic product with the three-dimensional additive printer by depositing printing ink to successively print layers on one another, said forming comprising depositing the hemostatic flowable with the three-dimensional additive printer to form at least one portion of at least one layer of the stack of layers.

Preferable but non-limiting aspects of such method of manufacturing an hemostatic product, taken alone or in combination, are the following:
  the at least one layer of the stack of layers is entirely made with the deposition of the hemostatic flowable.
  the hemostatic flowable is used in several layers of the stack of layers in order to obtain the hemostatic product (10).
  the hemostatic flowable is used to form all the layers of the stack of layers in order to obtain the hemostatic product (10).
  in step b), a plurality of hemostatic flowables are provided to the three-dimensional additive printer for use as printing inks, said hemostatic flowables having different compositions.
  the composition of the hemostatic powder forming the hemostatic flowable comprises:
    collagen of the fibrillar type comprising a content of fibrous collagen and/or fibrillar collagen of at least 70% by weight relative to the total weight of the collagen, said collagen being in an amount ranging from 75% to 96% by weight relative to the total weight of the composition of the hemostatic powder preferably ranging from 80% to 90% by weight;
    at least one monosaccharide in an amount ranging from 1% to 12.5% by weight relative to the total weight of the composition of the hemostatic powder, preferably an amount ranging from 2.5% to 7.5% by weight, and more preferably an amount ranging from 4% to 6% by weight.
  the composition of the hemostatic powder forming the hemostatic flowable further comprises at least one glycosaminoglycan in an amount ranging from 1% to 30% by weight relative to the total weight of the composition of the hemostatic powder, preferably ranging from 2% to 25% by weight, preferably an amount ranging from 4% to 15% by weight, more preferably an amount ranging from 5% to 12.5% by weight, and even more preferably an amount ranging from 8% to 10% by weight.

the composition of the hemostatic powder forming the hemostatic flowable further comprises at least one coagulation factor in an amount lower than 0.5% by weight relative to the total weight of the composition of the hemostatic powder, preferably in an amount lower than 0.1% by weight.

the saline solution used for forming the hemostatic flowable comprises at least one coagulation factor, said coagulation factor being in an amount ranging from 10 IU/mL to 5000 IU/mL of the saline solution, preferably ranging from 25 IU/mL to 2500 IU/mL of the saline solution, more preferably ranging from 50 IU/mL to 1000 IU/mL of the saline solution, and even more preferably ranging from 100 IU/mL to 500 IU/mL of the saline solution.

the mass of the saline solution used to form the hemostatic flowable is between 2 to 10 times of the mass of the hemostatic powder, and preferably between 4 to 5 times of the mass of the hemostatic powder.

the printing step c) is done at ambient atmosphere, preferably at ambient temperature.

after the hemostatic product has been formed in the printing step c), a coating step d) is performed wherein a solution including a coagulation factor, in particular thrombin, is used to coat an external surface of the hemostatic product.

the coating step d) is performed by spraying the solution including a coagulation factor on the external surface of the hemostatic product.

after the hemostatic product has been formed in the printing step c), a soaking step e) is performed wherein the hemostatic product is soaked in a solution including a coagulation factor, in particular thrombin.

the final step of manufacturing the hemostatic product consists in maintaining the printed hemostatic product in ambient atmosphere for a predetermined resting period, said predetermined resting period being preferably less than 10 minutes, more preferably less than 5 minutes, and even more preferably less than 1 minute.

the whole process is performed at ambient atmosphere without any stimulation of the hemostatic product, in particular without photo-stimulation or heat stimulation.

BRIEF DESCRIPTION OF THE DRAWINGS

Other characteristics and advantages of the invention will become clear from the following description which is only given for illustrative purposes and is in no way limitative and should be read with reference to the attached drawings on which.

DETAILED DESCRIPTION OF THE INVENTION

Figure 1:
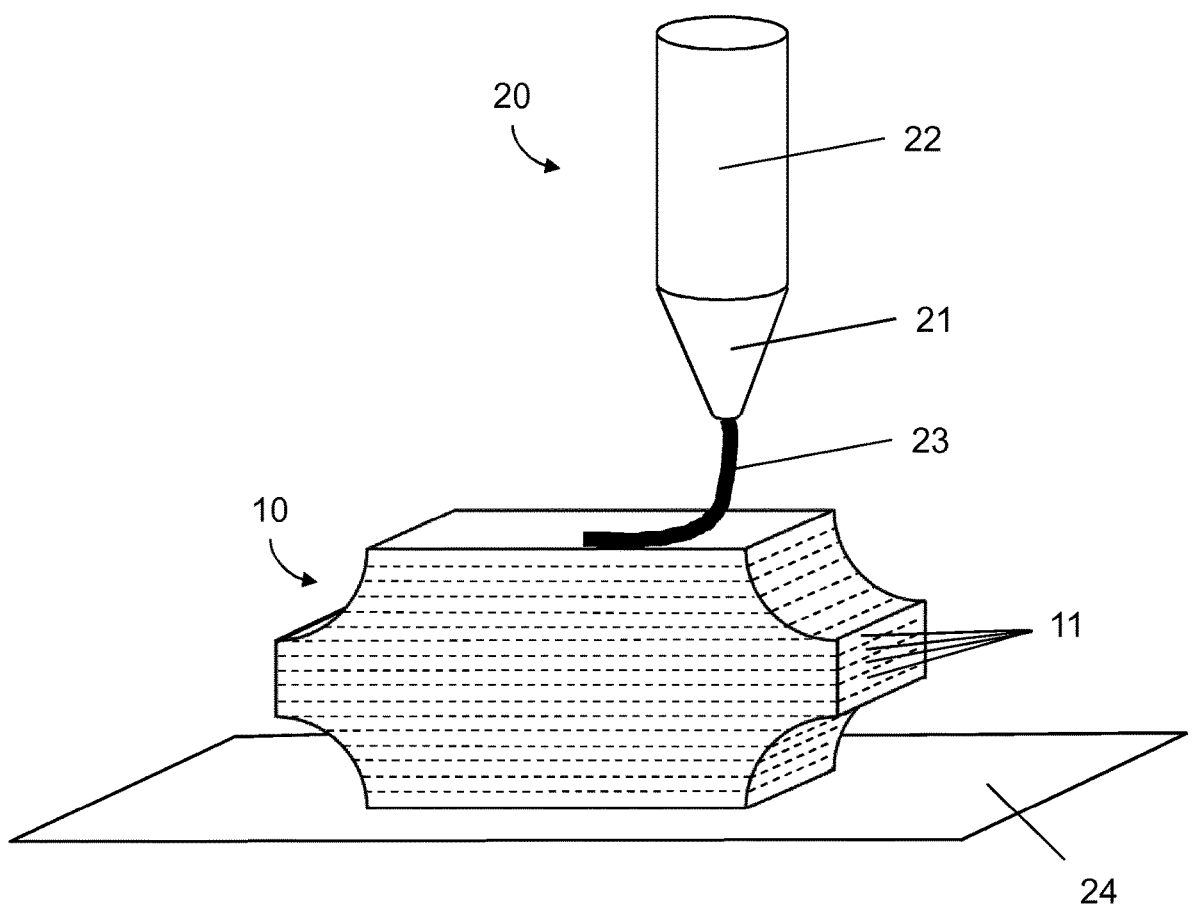
FIG. 1 is a schematic illustration of a three-dimensional (3D) hemostatic product being manufactured with a 3D additive printer using at least an hemostatic flowable as printing ink.

The inventors have surprisingly discovered that it was possible to manufacture a three-dimensional (3D) hemostatic product by using an hemostatic flowable as a printing ink in a three-dimensional printer, despite the fact that the hemostatic powder composition mixed with saline solution to form the hemostatic flowable is made of a collagen which is not cross-linked.

As will be apparent from the description below, the hemostatic flowable has a structure which enables an easy deposition with a 3D printer, and a good cohesion of the product formed by successive layers naturally joining together when deposited on one another.

In the following description, absent a statement to the contrary, weight percentages are given relative to the total dry weight of the composition of one product, e.g. of the hemostatic powder or of the hemostatic flowable or of the hemostatic product defined in this disclosure.

In the context of the present invention, "total dry weight of the composition of the hemostatic powder" and "total dry weight of the composition of the hemostatic powder" refer to the total weight of the composition of the hemostatic powder free of solvent, in particular water, and thus the total weight relative to the anhydrous product.

Similarly, in the context of the present invention, "total dry weight of the composition of the hemostatic flowable" and "total dry weight of the composition of the hemostatic flowable" refer to the total weight of the composition of the hemostatic flowable free of solvent, in particular water, and thus the total weight relative to the anhydrous product.

Similarly, in the context of the present invention, "total dry weight of the composition of the hemostatic product" and "total dry weight of the composition of the hemostatic product" refer to the total weight of the composition of the hemostatic product free of solvent, in particular water, and thus the total weight relative to the anhydrous product.

In addition, the weights of the components and the resulting percentages can correspond to the anhydrous weight of these components, in other words, to the weight of the component not including the water which it could contain. This can also be applied to the percentages obtained.

The composition of the hemostatic powder used for forming the hemostatic flowable can comprise a collagen content greater than or equal to 70% by weight relative to the total weight of the composition of the hemostatic powder, in particular greater than or equal to 75% by weight, in particular greater than or equal to 77% by weight, indeed greater than or equal to 80% by weight.

In addition, the composition of the hemostatic powder can comprise a collagen content less than or equal to 99% by weight relative to the total weight of the composition of the hemostatic powder, in particular less than or equal to 96% by weight, in particular less than or equal to 93% by weight, indeed less than or equal to 90% by weight.

Thus, the composition of the hemostatic powder can comprise a collagen content ranging from 70% to 99% by weight relative to the total weight of the composition of the hemostatic powder, in particular ranging from 75% to 96% by weight, in particular ranging from 77% to 93% by weight, indeed ranging from 80% to 90% by weight. Preferably, the content of collagen is around 86% by weight of the total weight of the composition of the hemostatic powder.

Collagen is the main structure protein in mammals. Collagen consists of tropocollagen (TC) molecules that have lengths around 280-300 nm and diameters of around 1.5 nm.

The term "fibrous collagen" refers to collagen in the form of fiber, corresponding to an assembly of fibrils. Fibers generally have a diameter ranging from 1 μm to 10 μm. The term "fibrillar collagen" refers to collagen in the form of fibrils. More precisely, fibrils generally have a diameter of 10 nm to 1 µm. Thus, fibrils are formed from staggered arrays of tropocollagen molecules, and these fibrils may be arranged to form collagen fibers. Fibrous and/or fibrillar collagen is generally not soluble, whereas non-fibrillar collagen is highly soluble.

The definition of fibrous collagen and fibrillar collagen can be in particular that given by Markus Buehler in "Nature designs tough collagen: explaining the nanostructure of collagen fibrils," in PNAS, Aug. 15, 2006, vol. 103, no. 33, pp. 12285-12290.

More than 28 different collagens have been discovered and are classified in 3 main categories: collagens of the fibrillar type, collagens of the non-fibrillar type, and FACIT collagens.

Collagens of the fibrillar type are collagens that mostly comprise fibrillar and/or fibrous collagens and hardly any non-fibrillar collagens (for example collagen of type I). Similarly, collagens of the non-fibrillar type are collagens that mostly comprise non-fibrillar collagens. Some collagens of the non-fibrillar type may consist only in non-fibrillar collagens (for example collagen of type IV or V).

The industrial extraction and purification of collagen generally consists in the destructuration of the initial tissues to 1) remove every or the majority of contaminant proteins and 2) to obtain the requested structuration level depending on the final use of the product. Collagen extraction is generally performed in acid or basic conditions that allow the solubilisation of monomolecular soluble collagen which is not fibrillar. The final collagen naturally contains a mix of fibrillar/fibrous collagen and non-fibrillar collagen. The proportion between fibrillar/fibrous collagen and non-fibrillar collagen depends on the tissue chosen for the extraction and the extraction process.

The final product is different than a collagen that has been obtained by an artificial mix of only fibrillar collagen and only non-fibrillar collagen. In the article entitled "Extraction of collagen from connective tissue by neutral salt solutions" (Proceedings of the NATIONAL ACADEMY OF SCIENCES Volume 41 Number I Jan. 15, 1955 by Jerome Gross, John H. Highberger and Francis O. Schmitt), are shown the differences between fibrillar and non-fibrillar collagens obtained after a specific extraction process which leads—as described previously—to a mix of those two collagens.

In the hemostatic powder used for forming the hemostatic flowable, the collagen is of the fibrillar type, and comprises fibrous and/or fibrillar collagen in an amount of at least 60% by weight, in particular at least 70% by weight, in particular at least 75% by weight, indeed at least 80% by weight relative to the total weight of the collagen.

More particularly, the collagen comprises at least 85%, in particular at least 90%, in particular at least 95%, indeed at least 98% by weight of fibrous and/or fibrillar collagen relative to the total weight of the collagen in the composition of the hemostatic powder.

Preferably the composition comprises a content of fibrous and/or fibrillar collagen ranging from 85% to 95% by weight relative to the total weight of the collagen in the composition, and most preferably from 85% to 90% by weight.

This means that in the preferred embodiment, the composition of the hemostatic powder thus comprises a content of non-fibrillar collagen ranging from 5% to 15% by weight relative to the total weight of the collagen in the composition, and most preferably from 10% to 15% by weight.

It is very advantageous to have a composition with such proportion of fibrous and/or fibrillar collagen relative to the non-fibrillar collagen, in particular for use as a hemostatic powder preparation. Indeed, the fibrous and/or fibrillar collagen should be present in a sufficient amount to perform the hemostasis, and the non-fibrillar collagen should also be in a sufficient amount for the cohesion of the product and not in a too large amount to avoid excess of swelling.

The collagen can be selected among type I collagens or type I and III collagens. The collagen can be extracted from various source tissues, in particular skin and/or tendons, from all species, more particularly porcine, bovine or equine species.

The collagen can mostly be made of fibrous collagen of porcine origin extracted from skin and/or tendons. In the case of collagen extracted from tendons, the extraction can be such as described in international application WO 2010/125086.

The aforesaid collagen, in particular fibrous and/or fibrillar collagen, can come from acid or basic extraction. According to a particular embodiment, said collagen comes from basic extraction. According to a particular embodiment, the collagen can be such as described in patent application FR2944706.

Preferably, the collagen comes from a basic extraction that enables maximizing the content of fibrous and/or fibrillar collagen in the extracted collagen. Further, such basic extraction can be optimized for controlling the proportion of the fibrillar/fibrous collagen and the non-fibrillar collagen within the extracted collagen. Unlike the acidic extraction, the basic extraction allows the hydrolysis of proteoglycans. This action leads to the destructuration of the tissue and the separation of the fibers without modification of their shape. In acidic conditions, the swelling of the inner collagen molecules in the fibers leads to their partial destructuration during the process with the release of greater amount of non-fibrillar soluble collagen.

The collagen can be used as it is after extraction, i.e. without further treatment, or it can be cross-linked, notably by classic modes of cross-linking such as thermal dehydration, the use of bridging agents, for example formaldehyde and/or glutaraldehyde; by oxidized polysaccharides, for example according to the method described in international application WO 2010/125086; and/or by oxidized amylopectins or glycogen. Cross-linking the collagen is however not preferred as it complexifies the manufacturing process, without necessarily increasing the hemostatic efficacy.

Preferably, the collagen used in the composition does thus not undergo any further treatment, and in particular it is not cross-linked. Using non-cross-linked collagen has notably the advantage of simplifying the manufacturing process.

Using non-crosslinked collagen in the hemostatic flowable that can be used for forming the hemostatic product is also very advantageous as it limits the leaching out of chemicals during product degradation which could enhance the toxicity of the product. The resorption of the final product will be faster, and there will be no toxic intermediate-products during such resorption.

The composition of the hemostatic powder used for the hemostatic flowable further comprises at least one monosaccharide, alone or in mixture with other monosaccharides. Said monosaccharides can be selected from ribose, sucrose, fructose, glucose and mixtures thereof. The monosaccharide present in the hemostatic composition, alone or in mixture with monosaccharides, is in particular glucose.

The composition of the hemostatic powder can comprise a monosaccharide content ranging from 1% to 12.5% by weight relative to the total weight of the composition, in particular ranging from 1.5% to 10% by weight, in particular ranging from 2% to 8% by weight, and quite particularly ranging from 2.5% to 7.5% by weight. Most preferably, the monosaccharide content is around 5% by weight relative to the total weight of the composition.

The composition of the hemostatic powder can comprise a collagen/monosaccharide weight ratio ranging from 5 to 100, in particular from 7 to 65, more particularly from 10 to 50, and still more particularly from 11 to 40. Most preferably, the composition comprises a collagen/monosaccharide weight ratio of around 19.

The monosaccharide, notably ribose, sucrose, fructose, glucose and mixtures thereof, and in particular glucose, can notably make it possible to obtain particles comprising mainly fibrous and/or fibrillar collagen and monosaccharides with the desired characteristics, notably of size and density. Incorporation of monosaccharide in the mixture of collagen further allows reduction of the electrical charges within the composition, which enables forming a powder adapted to be placed within container such as tubes, blower, spraying or application dispensers. This also eases the formation of an hemostatic flowable by mixing such hemostatic powder with a saline solution, the resulting hemostatic flowable having properties particular advantageous for its use as a printing ink for a 3D additive printer.

Quite particularly, the presence of monosaccharide can make it easier and/or cheaper to obtain particles of a desired density and/or size, in particular in terms of improving the hemostatic properties of a powder of the composition.

Grounding collagen fibers without any additives leads to the reduction of the size of the fibers and lowers the density of the powder. Further, the final preparation contains important amount of electrical charges that prevent the manipulation of the final product. Adding monosaccharide before grinding of the collagen leads to a hardening of the preparation to mix allowing a rapid grinding (limitation of denaturation), thus enabling preparation of a powder with reduced electrical charges (suitable for placing the powder into containers, such as dispensers) and a final density suitable for applying and reconstituting the composition. As mentioned above, this also enables using such hemostatic powder to form hemostatic flowables with specific properties advantageously adapted for additive printing, in particular in terms of dimensions and density of the particles, but also with respect to the rheology of the hemostatic flowable.

Unlike what could have been expected such adjunction of monosaccharide has no effect on the final activity of the product. In particular, it does not modify the bioactivity of the final product. The monosaccharide has no hemostatic effects.

Further, such adjunction of the monosaccharide does not make it behaving as a foaming agent as it is the case in WO 01/97873. In WO 01/97873, the heating of the diluted solution leads to the formation of gelatin. High concentration of gelatin can be made to obtain very concentrated solution, but the final product contains gelatin and not collagen. Gelatin is known to be less hemostatic than collagen as platelet aggregation needs the presence of collagen fibrils and structure of the native collagen which are absent in gelatin.

According to one embodiment, the composition comprises, preferably consists of, particles comprising, preferably consisting of, collagen and monosaccharide, notably selected from ribose, sucrose, fructose, glucose and mixtures thereof, in particular glucose.

The composition can comprise at least one coagulation factor. Said coagulation factors are well known to those persons skilled in the art. Preferably, one of the coagulation factors is thrombin. Even more preferably, the composition of the hemostatic powder comprises only thrombin as coagulation factor.

Said coagulation factor, in particular thrombin, can come from animal sources (extracted from animal tissues and fluids) or from recombinant sources (produced by cultures of genetically modified cells). The coagulation factor may for example be thrombin extracted from human tissues and fluids.

When a coagulation factor, in particular thrombin, is present, its content is preferably less than 0.5% by weight relative to the total weight of the composition of the hemostatic powder, preferably less than 0.1% by weight.

In the case of thrombin, international units (IU) are generally used. Thus, the composition can comprise a thrombin content ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg. Most preferably the content of thrombin—if any—is around 0.83 IU/mg of the composition.

In addition to the mix of collagen and monosaccharide, the composition can comprise at least one other carbohydrate compound, which can be a glycosaminoglycan. Such carbohydrate compound may be part of the composition, with or without a coagulation factor such as thrombin.

Said glycosaminoglycan can be selected from chondroitin sulfates, dermatan sulfate, hyaluronic acid and mixtures thereof, in particular chondroitin sulfates.

Glycosaminoglycans can make it possible to improve the speed at which blood is absorbed by the hemostatic composition. More particularly, glycosaminoglycans can accelerate contact between the blood and the hemostatic products, in particular collagen and thrombin.

The composition can comprise a glycosaminoglycan content ranging from 1% to 30% by weight relative to the total weight of the composition, in particular ranging from 2% to 25% by weight, in particular ranging from 3% to 20% by weight, in particular ranging from 4% to 15% by weight, quite particularly ranging from 5% to 12.5% by weight. Most preferably the content of glycosaminoglycan—if any—is around 9% by weight of the total weight of the composition.

The composition can comprise a collagen/glycosaminoglycan weight ratio ranging from 2.5 to 50, in particular from 3.5 to 35, more particularly from 5 to 25, and still more particularly from 6.5 to 20.

According to one embodiment, the composition comprises at least one, in particular one, monosaccharide and at least one, in particular one, glycosaminoglycan, notably such as defined above, and in particular in the amounts defined above.

The carbohydrate compounds are quite particularly monosaccharides and glycosaminoglycans.

The composition can comprise a carbohydrate content ranging from 2% to 25% by weight relative to the total weight of the composition, in particular ranging from 5% to 23% by weight, in particular ranging from 7% to 21% by weight, quite particularly ranging from 10% to 18% by weight.

The composition can comprise a collagen/carbohydrate compound weight ratio ranging from 2 to 40, in particular from 2.5 to 30, more particularly from 3 to 20, and still more particularly from 3.5 to 15.

The expression "total weight of carbohydrate compounds" refers to the sum of the weight of the monosaccharides defined above and the weight of the other carbohydrate compounds mentioned above.

According to one embodiment, the composition comprises, preferably consists of:
- collagen comprising mainly a fibrous and/or fibrillar collagen content of at least 50% by weight relative to the total weight of the collagen, and
- at least one, in particular one, monosaccharide.

Quite particularly, the composition comprises, preferably consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen comprises a fibrous and/or fibrillar collagen content of at least 50% by weight relative to the total weight of the collagen, and
- at least one monosaccharide, in particular glucose, in an amount ranging from 1% to 12.5% by weight relative to the total weight of the composition, notably ranging from 1.5% to 10% by weight, in particular ranging from 2% to 8% by weight, and quite particularly ranging from 2.5% to 7.5% by weight.

According to another embodiment, the composition comprises, preferably consists of:
- collagen comprising mainly a fibrous and/or fibrillar collagen content of at least 50% by weight relative to the total weight of the collagen,
- at least one, in particular one, monosaccharide,
- at least one, in particular one, coagulation factor.

Quite particularly, the composition comprises, preferably consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen content comprises a fibrous and/or fibrillar collagen content of at least 50% by weight relative to the total weight of the collagen,
- at least one monosaccharide, in particular glucose, in an amount ranging from 1% to 12.5% by weight relative to the total weight of the composition, in particular ranging from 1.5% to 10% by weight, in particular ranging from 2% to 8% by weight, and quite particularly ranging from 2.5% to 7.5% by weight, and
- at least one, in particular one, coagulation factor, in particular thrombin, in an amount ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg.

According to another embodiment, the composition comprises, preferably consists of:
- collagen comprising mainly a fibrous and/or fibrillar collagen content of at least 50% by weight relative to the total weight of the collagen,
- at least one, in particular one, monosaccharide, and
- at least one, in particular one, glycosaminoglycan.

Quite particularly, the composition comprises, preferably consists of:
- collagen, notably in an amount ranging from 70% to 99% by weight relative to the total weight of the composition, in particular ranging from 75% to 96% by weight, in particular ranging from 77% to 93% by weight, indeed ranging from 80% to 90% by weight, wherein said collagen content comprises a fibrous and/or fibrillar collagen content of at least 50% by weight relative to the total weight of the collagen,
- at least one monosaccharide, in particular glucose, in an amount ranging from 1% to 10% by weight relative to the total weight of the composition, in particular ranging from 1% to 12.5% by weight, in particular ranging from 1.5% to 10% by weight, in particular ranging from 2% to 8% by weight, and quite particularly ranging from 2.5% to 7.5% by weight, and
- at least one glycosaminoglycan, in particular chondroitin sulfate, in an amount ranging from 1% to 30% by weight relative to the total weight of the composition, in particular ranging from 2% to 25% by weight, in particular ranging from 3% to 20% by weight, in particular ranging from 4% to 15% by weight, quite particularly ranging from 5% to 12.5% by weight.

According to still another embodiment, the composition comprises, preferably consists of:
- collagen comprising a fibrous and/or fibrillar collagen content of at least 50% by weight relative to the total weight of the collagen,
- at least one, in particular one, monosaccharide,
- at least one, in particular one, coagulation factor, and
- at least one, in particular one, glycosaminoglycan.

Quite particularly, the composition comprises, preferably consists of:
- collagen, notably in an amount ranging from 70% to 99% by weight, in particular ranging from 75% to 96% by weight, in particular ranging from 77% to 93% by weight, indeed ranging from 80% to 90% by weight relative to the total weight, in particular to the dry weight, of the composition, wherein said collagen comprises a fibrous and/or fibrillar collagen content of at least 50% by weight relative to the total weight of the collagen,
- at least one monosaccharide, in particular glucose, in an amount ranging from 1% to 10% by weight relative to the total weight of the composition, notably ranging from 1% to 12.5% by weight, notably ranging from 1.5% to 10% by weight, in particular ranging from 2% to 8% by weight, and quite particularly ranging from 2.5% to 7.5% by weight,
- at least one coagulation factor, in particular thrombin, in an amount ranging from 0.01 IU/mg to 20 IU/mg of the composition, in particular from 0.05 IU/mg to 10 IU/mg, in particular from 0.1 IU/mg to 5 IU/mg, indeed from 0.2 IU/mg to 2 IU/mg, and
- at least one glycosaminoglycan, in particular chondroitin sulfate, in an amount ranging from 1% to 30% by weight relative to the total weight of the composition, in particular ranging from 2% to 25% by weight, notably ranging from 3% to 20% by weight, in particular ranging from 4% to 15% by weight, quite particularly ranging from 5% to 12.5% by weight.

According to a quite particular embodiment, the composition comprises, preferably consists of:
- collagen of the fibrillar type, mostly comprising fibrous and/or fibrillar collagen, said collagen of the fibrillar type being for example obtained by extraction in basic medium, and being in an amount of around 85% by weight relative to the total weight of the composition,
- glucose, in an amount of around 4.9% by weight relative to the total weight of the composition,
- thrombin, in an amount of 0.2 IU/mg to 2 IU/mg of the composition, and
- chondroitin sulfate, in an amount of around 10% by weight relative to the total weight of the composition.

According to another particular embodiment, the composition comprises, preferably consists of:

collagen of the fibrillar type, mostly comprising fibrous and/or fibrillar collagen, said collagen of the fibrillar type being for example obtained by extraction in basic medium, and being in an amount of around 85% by weight relative to the total weight of the composition, glucose, in an amount of 5% by weight relative to the total weight of the composition, and chondroitin sulfate, in an amount of 10% by weight relative to the total weight of the composition.

In the context of the present disclosure, the expression "an amount of around X %" refers to a variation of plus or minus 20%, in other words, an amount of around 10% means from 8% to 12%, in particular a variation of plus or minus 10%, indeed plus or minus 5%.

When the coagulation factor in form of powder, in particular thrombin, is added, such powder of the coagulation factor is preferably mixed with the powder of the homogeneous molecular mixture of collagen/monosaccharide already prepared.

When both a glycosaminoglycan (e.g. chondroitin sulfate) and a coagulation factor (e.g. thrombin) are added, they are preferably firstly mixed together, and this mix is added to the previous mixture of collagen/monosaccharide (already ground into powder).

The thrombin is not stabilized neither by carbohydrate nor collagen. The thrombin is never in contact with a solution of the monosaccharide (contrary to WO 98/57678) which prevents any denaturation of the protein and a rehydration of the powder leading to an impossibility to dry it again properly.

The composition in powder form can in particular comprise, or consist of:

particles comprising, or consisting of, collagen of the fibrillar type and at least one monosaccharide, in particular glucose, wherein in particular said particles have a size, granulometry and/or density such as defined in the present description, and optionally, particles comprising, or consisting of, at least one glycosaminoglycan, in particular chondroitin sulfates, and/or at least one coagulation factor, in particular thrombin, wherein in particular said particles have a size, granulometry and/or density such as defined in the present description.

As explained above, the proposed hemostatic powder has the advantage of allowing a grinding adapted to the use of the hemostatic powder, in particular a grinding to have particles of small dimensions, in particular lower than 500 µm, more preferably lower than 350 µm.

The composition of the hemostatic powder advantageously can for instance comprise at least 50% by weight of particles whose size is between 200 µm and 400 µm.

The particles constituting the hemostatic powder advantageously have a mean granulometry ranging from 10 µm to 500 µm, in particular from 50 µm to 400 µm.

Advantageously, at least 90% by weight, in particular 100% by weight, of the particles constituting said hemostatic powder can pass through a screen whose mesh is 500 µm, in particular 400 µm.

At least 90% by weight, and in particular at least 95% by weight, of the particles constituting said hemostatic powder can be retained by a screen whose mesh is 10 µm, notably 20 µm, indeed 30 µm, indeed 50 µm. For instance, at least 90% by weight, and preferably 90% by weight, of the particles constituting said hemostatic powder have a size larger 20 µm that can be retained by a screen whose mesh is 20 µm.

According to a specific example, the composition of the hemostatic powder is formed to comprise at least 50% by weight of particles whose size is lower than 200 µm, 90% by weight of particles whose size is lower than 350 µm, 98% by weight of particles whose size is lower than 400 µm. In this case, the particles constituting the hemostatic powder advantageously have a mean granulometry ranging from 20 µm to 300 µm, preferably from 25 µm to 270 µm. For instance, 80% by weight of particles constituting the hemostatic powder have a granulometry ranging from 20 µm to 300 µm. Such a specific example of the hemostatic powder is particularly advantageous to form an hemostatic flowable to be used in a 3D additive printer as is described in more details below.

The powder repartition is preferably chosen to allow the powder to be hydrated. With particles size too small, the powder does not form a hydrated matrix consistent with the specification and aspect required.

The hemostatic composition in powder form comprises in particular:

particles comprising collagen and a monosaccharide, and optionally, at least glycosaminoglycan and/or a coagulation factor such as thrombin.

The composition of hemostatic powder can comprise:

particles comprising collagen, a monosaccharide and optionally at least one glycosaminoglycan and/or coagulation factor, particles comprising collagen, a monosaccharide and optionally a coagulation factor and optionally glycosaminoglycan particles, particles comprising collagen and a monosaccharide and particles comprising at least one glycosaminoglycan and/or coagulation factor.

In the context of the present invention, the expression "dry powder" means that the composition comprises a limited content of solvent, in particular water. Said limited content can be less than 5% by weight, in particular less than 3% by weight, and quite particularly less than 1% by weight relative to the total weight of the composition.

Said dry form can be obtained by simple evaporation of the solvent used, by dehydration by organic solvents.

As indicated above, the described hemostatic powder is formed from non-cross-linked collagen because it is much simpler in terms of manufacturing process, and it has been proven to have a good efficacy with respect to hemostasis even though the collagen of the powder was not cross-linked.

The inventors have surprisingly discovered that, despite the fact that the collagen was not cross-linked, mixing the above described specific hemostatic powder with a saline solution enabled forming an hemostatic product with a rheology, in particular a viscosity, allowing its use to form complex 3D hemostatic product, using for instance the hemostatic flowable as the raw material deposited in successive layers by a 3D additive printer.

This was indeed not expected as it was on the contrary known that the preparation of an hemostatic collagen paste from a mixture of a collagen based powder and a saline solution needed the use of cross-link collagen to work and be stable. This has been in particular disclosed in the US patent published on Jan. 2, 1990 under the reference U.S. Pat. No. 4,891,359. Cross-linking is namely known to give stability to the molecules by adding chemical bonds to the corresponding molecular structure, those additional chemical bonds being usually required for the molecules to be in an aqueous form.

It was also not expected that such an hemostatic flowable could be used directly in a 3D printer to form a 3D hemostatic product, without necessarily having to adapt the printing process of conventional 3D additive printers, in particular the 3D printers working by extrusion.

Consequently, according to a preferred embodiment, the dry hemostatic powder as described above, where the collagen is not cross-linked, is thus to be hydrated, for example with a saline solution or with water, in order to form an hemostatic flowable, which will be used as a printing ink in a 3D printer.

The term "flowable" as used herein applies to compositions whose consistencies enable the composition to sustain a certain shape without any stress applied, while being deformable if a stress, such as pressure, is applied on the composition. The minimum shear stress required to initiate flow of the product corresponds to the yield stress.

A flowable is not a liquid, nor a sponge, nor a powder, rather a kind of paste, gel or matrix that presents a certain viscosity, such viscosity depending on the stress applied on the flowable.

Preferably the flowable has a viscosity comprised between 20 Pa·s and 10000 Pa·s (corresponding to a range of fluidity between 0.0001 (Pa·s)$^{-1}$ and 0.05 (Pa·s)$^{-1}$) when no stress or a low stress (e.g. lower than 10 Pa) is applied. The flowable can however have a higher viscosity for instance from 1000 Pa·s to 1000000 Pa·s for higher stress.

A flowable refers to a composition that is for instance capable of passing through a syringe and/or cannula. Advantageously, it can also pass through the nozzle of a printer head of a 3D printer as will be explained below.

In the present description, we refer indifferently to a hemostatic flowable, a flowable hemostat, and a hemostatic matrix to designate the same particular composition.

The mixing of the hemostatic powder and the saline solution is thus performed to make an hemostatic flowable as defined above, in which the hemostatic powder is suspended in water or in the saline solution.

The hemostatic powder used to manufacture the hemostatic flowable can be for example prepared according to a method comprising at least the following steps:
  a) formation of an aqueous suspension comprising, preferably consisting of, collagen of the fibrillar type—mainly comprising fibrous and/or fibrillar collagen—and a monosaccharide, such as glucose,
  b) recovery of the product in the form of precipitate, paste or gel, notably by centrifugation or decantation,
  c) drying of the product, for example by evaporation.
  d) grinding of the product to the desired particle-size, in particular by a hammer mill, and
  e) optionally, adding thrombin and/or chondroitin sulfates, notably in solid form, in particular in powder form.

The formation in step a) of an aqueous suspension comprising, the fibrous/fibrillar collagen and a monosaccharide leads to a homogeneous repartition of the monosaccharide around the collagen molecules. Further, the close contact between the molecular species of collagen and the monosaccharide leads, after dehydration, to a hard cake suitable for obtaining—by grounding—a powder with the required high density. On the contrary, mixing a collagen powder and a glucose powder does not lead to an homogeneous and sprayable powder, in particular because of the density and electrical charges.

In step a) the collagen can be present at a concentration ranging from 30 g/L to 150 g/L.

The monosaccharide can be added to the suspension or to the homogeneous collagen paste in an amount such as defined in the description, and more particularly from around 2% to 5% by weight relative to the weight of the collagen.

In step a) the monosaccharide can be present at a concentration ranging from 0.3 g/L to 10 g/L.

The aqueous suspension of collagen of step a) can be acid, and in particular comprise an acid such as hydrochloric acid. Said acid can be present at a concentration ranging from 0.01 M to 0.5 M, and in particular from 0.02 M to 0.1 M, indeed around 0.05 M. Said suspension can be in the form of homogeneous paste.

Step b) can comprise the pouring of the suspension into a mold.

Step c) is performed so as to obtain a cake as thick as possible (superior the final particle-size wanted), with a very high density and as less air bubbles as possible (less than 5%) inside the cake.

Step d) can be followed by a step of screening of the powder, notably in order to obtain the desired particle size.

According to a preferred embodiment, step a) consists in forming a mixture comprising 95% by weight of non-cross-linked collagen of the fibrillar type and 5% by weight of monosaccharide (e.g. glucose).

As mentioned above, a glycosaminoglycan (e.g. chondroitin sulfate) can be added to the mixture formed by the non-cross-linked collagen of the fibrillar type and monosaccharide. Preferably, such glycosaminoglycan is added in a mixture/glycosaminoglycan weight ratio ranging from 70/30 to 100/0, preferably a weight ratio of 80/20, or 85/15, or 90/10 or 95/5. Those weight ratios could be used for any type of mixture formed by non-cross-linked collagen of the fibrillar type and monosaccharide.

For instance, in a 95/5 weight ratio, the composition of the hemostatic powder can comprise 95% by weight of the mixture made of 95% of collagen and 5% of glucose, and 5% by weight of chondroitin sulfate. The hemostatic powder thus comprises 90.25% by weight of collagen and 4.75% by weight of glucose, and 5% by weight of chondroitin sulfate.

Alternatively, in a 85/15 weight ratio, the composition of the hemostatic powder can comprise 85% by weight of the mixture made of 95% of collagen and 5% of glucose, and 15% by weight of chondroitin sulfate. The hemostatic powder thus comprises 80.75% by weight of collagen, 4.25% by weight of glucose, and 15% by weight of chondroitin sulfate.

Alternatively, in a 80/20 weight ratio, the composition of the hemostatic powder can comprise 80% by weight of the mixture made of 95% of collagen and 5% of glucose, and 20% by weight of chondroitin sulfate. The hemostatic powder thus comprises 76% by weight of collagen, 4% by weight of glucose, and 20% by weight of chondroitin sulfate.

Alternatively, in a 90/10 weight ratio, the composition of the hemostatic powder can comprise 90% by weight of the mixture made of 95% of collagen and 5% of glucose, and 10% by weight of chondroitin sulfate. The hemostatic powder thus comprises 85.5% by weight of collagen, 4.5% by weight of glucose, and 10% by weight of chondroitin sulfate.

According to a specific example, the composition of the hemostatic powder used to manufacture the hemostatic flowable comprises chondroitin sulfate in a content of 10% by weight of the total weight of the mixture, such that the final composition comprises:
  collagen: 86.36% by weight relative to the total weight of the composition;

glucose: 4.54% by weight relative to the total weight of the composition;

chondroitin sulfate: 9.09% by weight relative to the total weight of the composition;

When thrombin is also added, it represents a final content lower than 0.01% by weight relative to the total weight of the composition. In the above mixture, thrombin may be in an amount of 0.083 IU/mg of the composition.

For all the aforesaid powder products, it is possible to apply a more or less thorough grinding to obtain a powder of variable particle-size according to the type of grinding and the duration thereof.

As explained, the hemostatic powder is then suspended in a saline solution. The saline solution is preferably a standard sterile saline solution used in operating room.

The composition of the saline solution can comprise monovalent or divalent chloride cations, such as calcium chloride or sodium chloride, in a concentration ranging from 0 to 300 mM, preferably a concentration ranging from 100 to 200 mM, especially a concentration of about 150 mM.

It is preferably composed of distilled water with an amount of sodium chloride between 0.5% and 1.5%, and preferably around 0.9%.

The saline solution is preferably pure, meaning that it consists of a mix of sodium chloride in distilled water, without the addition of any other components.

Alternatively, the saline solution can comprise a coagulation factor, such as thrombin. In this case, the hemostatic powder to be mixed with the saline solution does preferably not comprise any coagulation factor.

For instance, the coagulation factor is in an amount ranging from 10 IU/mL to 5000 IU/mL of the saline solution, preferably ranging from 25 IU/mL to 2500 IU/mL of the saline solution, more preferably ranging from 50 IU/mL to 1000 IU/mL of the saline solution, and even more preferably ranging from 100 IU/mL to 500 IU/mL of the saline solution.

The saline solution can be stored in different forms, such as bulk in a large container, or in a specific container of a determined volume.

Preferably, the saline solution is part of a kit to produce the hemostatic flowable, such a kit also comprising a specific amount of the hemostatic powder in a container.

The composition of the hemostatic flowable made from the hemostatic powder can comprise a dried non cross-linked fibrillar collagen content ranging from 60% to 99% by weight relative to the total weight of the composition, in particular ranging from 75% to 90% by weight, and quite particularly ranging from 83% to 88% by weight.

The composition of the hemostatic flowable made from the hemostatic powder can comprise a monosaccharide content, particularly glucose, ranging from 1% to 10% by weight relative to the total weight of the composition, in particular ranging from 3% to 7% by weight, and quite particularly ranging from 4% to 5% by weight.

The composition of the hemostatic flowable made from the hemostatic powder can comprise a glycosaminoglycan content (lyophilized, dried particles), particularly chondroitin sulfate, ranging from 1% to 30% by weight relative to the total weight of the composition, in particular ranging from 5% to 12% by weight, and quite particularly ranging from 8% to 10% by weight.

The composition of the hemostatic flowable made from the hemostatic powder can comprise a coagulation factor, preferably thrombin, in a content lower than 1% by weight relative to the total weight of the composition. Preferably, if a coagulation factor is present, its content is lower than preferably than 0.5% by weight relative to the total weight of the composition, preferably less than 0.1% by weight.

Possibly, the composition of the hemostatic flowable made from the hemostatic powder can comprise a cross-linking initiator, particularly oxidized glycogen or retinol, or a photo-initiator. Those initiators are not necessary for the manufacturing of the hemostatic product, but will rather be of use to later functionalize the hemostatic product. Such cross-linking initiator or photo-initiator is chosen to enable a reaction in the hemostatic product only upon a specific stimulus. In particular, for the cross-linking initiator, no cross-linking will occur spontaneously and the cross-linking initiator has to be activated.

The hemostatic flowable made from the hemostatic powder mixed with a specific amount of saline solution can be used as a hemostatic agent.

This hemostatic flowable can also be used as a pharmaceutical composition, in particular a hemostatic drug.

As aforementioned, the hemostatic flowable is suitable to make a 3D-hemostatic product, and can be advantageously used directly in a 3D printer.

Preferably the hemostatic flowable is usable as a raw material forming the printing ink in any kind of 3D printer, in particular the so-called bioprinter, for example 3D printers working by extrusion of the raw material.

In case the 3D printer comprises several printing heads, several printing inks of different composition are usually used, at least one of them being the proposed hemostatic flowable. In a particular case, several hemostatic flowables of different compositions will be used as printing inks in the 3D printer.

Regarding bioprinters, one can refer to the article of Ibrahim T. Ozbolat and Monika Hospodiuk entitled "Current advances and future perspectives in extrusion-based bio-printing" published in Biomaterials in 2015 (see Biomaterials 76(2016) 321-343) which is entirely incorporated by reference.

Before the hemostatic flowable is prepared for use in a 3D printer, all the active components can be contained all together, in a powder form, within a specific container. This is very advantageous for several aspects. It first eases the storage of the product, as one has to particularly take care of the container having the hemostatic powder, and not really of the saline solution, which is a commonly available product.

This is also very advantageous in terms of manufacturing as only the hemostatic powder has to be sterilized before storage, which would for example not be the case if some components were first mixed with a saline solution (e.g. thrombin), and then mixed to an hemostatic powder.

It has to be noted that if no coagulation factor such as thrombin is used in the hemostatic powder or in the saline solution, it could be considered adding this coagulation factor at the end of the manufacturing of the hemostatic product.

In this respect, the hemostatic product could for example be soaked in a solution comprising a coagulation factor.

A solution comprising a coagulation factor could also be used to coat the external surface of the hemostatic product. Such coating coudl for instance be done by spraying said solution on the external surface of the hemostatic product.

Possibly, as it will be explained, the hemostatic product made by 3D-printing can also be sterilized at the end of the manufacturing process, and thus the hemostatic powder would not need to be sterilized.

The container could have the form of a cartridge directly usable in the 3D printer.

Preferably, for preparing an hemostatic flowable to be used for manufacturing a 3D hemostatic product with a 3D additive printer, the mass of saline solution to be used for hydrating the hemostatic composition is between 2 and 10 times of the mass of the hemostatic powder, preferably between 4 and 5 times of the mass of the hemostatic powder.

The proposed hemostatic flowable has the advantage of having a rheology to insure printability with the bioprinter.

In particular, the hemostatic flowable has particles with dimensions sufficiently low to pass through the printing head of the printer and avoid blockages in the printer nozzle (typically lower than 400 µm).

Preferably, the yield stress of the hemostatic flowable is comprised between 500 Pa and 20000 Pa, preferably less than 15000 Pa, even more preferably between 1000 Pa and 3000 Pa.

The amount of hemostatic powder for a printing ink cartridge can be between 1 g and 2 g.

The amount of saline solution in such printing ink cartridge is then between 4 mL and 10 mL, more preferably between 5 mL and 10 mL.

According to a preferred example, the printing ink of a printing ink cartridge is an hemostatic flowable made with 1.65 g of hemostatic powder mixed with 7 mL of pure saline solution.

It can be considered providing printing ink cartridges of larger volume (in particular if the 3D hemostatic product to be printed has a large volume), but the ratio between the amount of hemostatic powder and saline solution to form the hemostatic flowable will preferably remain the same as above. For example, the printing ink cartridge includes an hemostatic flowable made with 16.5 g of hemostatic powder mixed with 70 mL of pure saline solution.

While transferring the saline solution into the container containing the hemostatic powder, said container is preferably rotated, for instance around its own axis, in order to ease the incorporation of the saline solution into the hemostatic powder. If the saline solution is incorporated manually by a user, the rotation of the container can also be done by hand. The process could however be automated in required.

Tapping and/or slightly shaking the container while transferring the saline solution could also be advantageous to promote incorporation of the saline solution into the hemostatic powder.

Once the saline solution is transferred into the container, the container is closed and agitated to mix the hemostatic powder with the saline solution. The agitation can be performed by mixing the components with a spatula or by shaking.

The agitation is preferably done for a duration between 5 seconds and 60 seconds, even more preferably at least 30 seconds, for example 20 seconds. A shaking time of between 10 second to 30 seconds, for example 20 seconds, is however already efficient in terms of hydration of the hemostatic powder.

The shaking is preferably performed by hand but could also be automated.

When done manually, the mixing or shaking could consist in moving the container up and down a certain amount of times. For instance, the dispenser could be moved up and down at least between 10 to 30 times, preferably 20 times. To increase the efficiency of the mixing, the dispenser could also be flipped over and then moved up and down a certain amount of times. In this second phase of manual mixing, the dispenser 1 could also be moved up and down at least between 10 to 30 times, preferably 20 times.

After the shaking, the container enclosing the hemostatic flowable having been formed is preferably left to stand for at least of 30 seconds, preferably at least of 60 seconds, and even more preferably at least of 90 seconds.

The standing time is likely to be between 30 seconds and 120 seconds, preferably around 90 seconds.

This rest period enables the hydration of the hemostatic powder and initial swelling to form the hydrated hemostatic flowable.

The hemostatic flowable can be prepared at room temperature and stand for one minute to a few hours. A maximal swelling can be reached in less than 5 minutes.

The above preparation of the hemostatic flowable can be done directly in a cartridge to be used in the bioprinter or in an intermediate container before the hemostatic flowable is transferred into a printing cartridge.

The hemostatic flowable thus formed has the advantage of being homogeneous. In particular, the hemostatic flowable has substantially an homogeneous fluidity within the container. This is particularly advantageous as the deposition of the hemostatic flowable will thus be identical whether it is the beginning of the material from the container or the remaining of the material.

Once the hemostatic flowable has been formed through hydration of the hemostatic powder with the saline solution, the hemostatic flowable is usable for a few hours, e.g. at least 8 hours, without any loss of properties or performance.

FIG. 1 schematically illustrates the manufacturing of a 3D hemostatic product using a 3D additive printer 20 from which only the depositing nozzle 21 and the body of a printing ink container 22 are represented.

The printing process is preferably done at ambient atmosphere, at room temperature.

The process has the advantage of allowing an impression of the 3D hemostatic product directly in an operating room for instance. The printing process can be of course also done in any other rooms, in particular outside of an operating room, and independently of any surgical operation.

Alternatively, the 3D hemostatic product could be directly printed on a surface of a patient to be treated, for instance directly on a bleeding area or a bleeding wound of a patient being operated.

It is however not necessary to print the hemostatic product directly on a surface of a patient to be treated. The printing process can be done without a patient, outside of a patient, in particular outside of any surgical area of a patient.

The nozzle 21 of the 3D printer 20 is used to deposit the hemostatic flowable 23 from the printing ink container 22 onto a support 24 and form successive layers 11 onto one another to produce a 3D hemostatic product 10.

The 3D printer is controlled to produce a spatial patterning of raw material, comprising—and preferably consisting of—the hemostatic flowable, and assemble it using a computer-aided layer-by-layer deposition approach for fabrication of the 3D hemostatic product 10.

Preferably, the 3D hemostatic product that is to be manufactured has a shape that can be defined by a three-dimensional model which is provided as an input data to the 3D additive printer 20.

The 3D additive printer 20 usually comprises a processing unit that is configured to process the 3D model to define a printing pattern with a plurality of layers designed to be stacked on one another so as to form a stack of layers corresponding to the 3D model. This printing pattern will also depend on the raw material to be used as printing ink and the nature of the 3D hemostatic product to be manufactured.

The simplest 3D hemostatic product is indeed made of a single material, i.e. the hemostatic flowable, arranged in a stack of layers that are naturally joined together (it is said that the layers are added together). By naturally joined together, it is meant that there is no need of a further active process to have two adjacent layers be joined together, in particular no cross-linking is needed.

The layers that are printed on one another are joined together by self-assembly. There is no cross-linking phenomena and no covalent bounds created between the layers.

Indeed, the proposed hemostatic flowable used for the printing of the hemostatic product has a high concentration in polymers (due to the concentration in collagen) that promotes this self-assembly.

In addition, the proposed hemostatic flowable is mainly composed of non-cross-linked collagen of the fibrillar type which further promotes this self-assembly.

Finally, the proposed hemostatic flowable has thixotropic properties that enables a self-assembly particularly interesting for the manufacturing of product through printing.

When the bioprinter exerts on the proposed hemostatic flowable a constraint that is above the yield stress, the viscosity of such hemostatic flowable will decrease, enabling the printing process. Such phenomenon is referred to shear thinning.

After such a shearing stress imparted by the printer, the proposed hemostatic flowable has thixotropic properties that enables returning to its original, unconstrained, more viscous and stable state in a predetermined time which is sufficiently long for another layer to be printed onto a first layer while allowing mixing of the material used to print those layers, and sufficiently short for the printed product to be quickly cohesive and stable.

Preferably, after deposition, the proposed hemostatic flowable returns to its original unconstrained state in less than 10 minutes, more preferably less than 5 minutes, even more preferably less than 1 minute or less than 30 seconds.

It could also be considered to have a 3D hemostatic product where only one of the external layers of the stack of layers, or both external layers (the upper layer and the bottom layer) are made by deposition of the hemostatic flowable, whereas some or all of the intermediate layers sandwiched between the external layers are made from another material which is also adapted to be deposited with the 3D printer.

For instance, it could be considered forming an artificial body part with the 3D printer (e.g. a portion of tendon, cartilage, meniscus, intervertebral disc, etc.) and having it coated with the hemostatic flowable to improve its implantation within the body of the patient and the corresponding healing process.

To avoid that only the upper and bottom layers of the 3D product have hemostatic properties (which is the case when only those external layers are made with the hemostatic flowable), the printing process can be controlled so that each layer can be made of several printing inks. Thus, it will be possible to form the intermediate layers with a peripheral part made with the hemostatic flowable. This way of additive printing enables manufacturing a 3D product with an envelope (external walls) having hemostatic properties whereas the core of the 3D product can be made of a different material.

It could also be considered forming 3D hemostatic products with different printing inks made of hemostatic flowables of different compositions. This would for instance be useful to propose multilayers products with layers of different hemostatic properties.

Advantageously, the 3D additive printer 20 can be an extrusion printer equipped with multiple nozzle dispensers, each nozzle dispenser being associated with a different printing ink. It presents the advantage of allowing to print conveniently the 3D hemostatic product made from different layers, wherein each layer can be composed of different compositions contained in different printing cartridges. In particular, one layer can have several portions being each printed with a different printing ink, in particular different hemostatic flowables.

Moreover, each layer of the 3D hemostatic product can be made of a different pattern, and superposing layers can be printed in various orientations and patterns.

The 3D hemostatic product 10 can be made by superposing two-dimensional (2D) layers.

As indicated above, a 2D layer can be made with various hemostatic flowable compositions forming several portions of the layer.

Advantageously, a 2D layer can be formed to have a hemostatic gradient, by forming several portions with several hemostatic flowable having different hemostatic powers.

As indicated above, 2D layers can be printed with various patterns, for instance curved lines, circles, polygons, dots, waves.

Between superposed layers or within a layer, patterns can have different orientations, for instance, patterns can be oriented perpendicularly, or in diagonal following various angles. Moreover, within a layer, the distance between patterns can also vary.

The superposed layers can moreover have different thickness, shapes and dimensions.

A 2D layer can be completely filled, or alternatively present voids

As a consequence, hemostatic products with complex shapes can be printed. Those printed hemostatic products can also have areas with a specific function, and several areas with different functions.

The printed hemostatic product can also be prepared so as to have a shape that can vary over time, for instance upon hydration. More precisely, the printed hemostatic product is a 3D hemostatic product, i.e. a product having a shape according to three spatial dimensions, with a fourth dimension corresponding to the transformation of the product over the time. Such 3D printed products with a fourth dimension are also referred to 4D products.

One can refer to the article of A. Sydney Gladman et al. entitled "Biomimetic 4D printing" published in Nature Materials in 2016 (see Nature Materials volume 15, pages 413-418 (2016)) which is entirely incorporated by reference.

This allows for instance to produce a 3D hemostatic product in which each layer, or at least two different layers, can have different hemostatic and/or swelling properties, for instance upon hydration.

The composition of the final printed hemostatic product can comprise a fibrillar collagen content, preferably a partially fibrillar collagen content, ranging from 60% to 99% by weight relative to the total weight of the composition, in particular ranging from 75% to 90% by weight, and quite particularly ranging from 83% to 88% by weight.

The composition of the printed hemostatic product can comprise a monosaccharide content ranging from 1% to 10% by weight relative to the total weight of the composition, in particular ranging from 3% to 7% by weight, and quite particularly ranging from 4% to 5% by weight.

The composition of the printed hemostatic product can comprise a glycosaminoglycan content ranging from 1% to 30% by weight relative to the total weight of the composition, in particular ranging from 5% to 12% by weight, and quite particularly ranging from 8% to 10% by weight.

The composition of the printed hemostatic product can comprise a coagulation factor, preferably thrombin, in a content lower than 1% by weight relative to the total weight of the composition. Preferably, if a coagulation factor is present, its content is lower than preferably than 0.5% by weight relative to the total weight of the composition, preferably less than 0.1% by weight.

The presence of collagen in the hemostatic flowable used to make the 3D-hemostatic product is necessary for the product cohesion, especially the cohesion between the different layers of the product. The use of non cross-linked fibrillar collagen is particularly advantageous. In addition, using fibrillar collagen helps promoting hemostasis.

As mentioned above, the hemostatic flowable has a high concentration in polymers (corresponding to the concentration of collagen) which promotes the printing process and enables manufacturing hemostatic products by a self-assembling manufacturing process. In particular, it enables manufacturing printed hemostatic products that are cohesive, self-supporting, and resistant without the need of a further reinforcing step, for example through natural or forced cross-linking, with photo-stimulation or heat-stimulation for instance.

As previously explained, monosaccharides, and particularly glucose, are conveniently used for preparing the hemostatic powder, in particular since it reduces electrical charges within the composition.

Moreover, monosaccharide can also be used for its hydrophilicity and are typically charge-polarized and capable of hydrogen bonding. This makes these molecules soluble not only in water but also in other polar solvents. Monosaccharide can also be useful for preservation of the possible coagulation factor.

Glycosaminoglycans, and especially chondroitin sulfates, are very hydrophilic too. The proportion of glycosaminoglycans in the composition of the hemostatic flowable used for the manufacturing of the printed hemostatic product makes the swelling properties of the printed product vary. More precisely, it influences the swelling properties of the pattern made with the specific hemostatic flowable.

It can be particularly advantageous to print an hemostatic product made of a superposition of layers with different concentrations in chondroitin sulfates, since chondroitin sulfates promote the product deformation upon hydration through swelling.

For instance, layers rich in chondroitin sulfates may swell more than layers mainly made of collagen and poorer in chondroitin sulfates. Variation in hydration and swelling across the printed hemostatic product can be used to deform and/or expand the hemostatic product upon hydration, in order to cover a bleeding wound for instance.

Use of glycosaminoglycans, and especially chondroitin sulfates, in the hemostatic flowable is also advantageous as it helps the printing process. More precisely, it appears that it promotes the flowing of the hemostatic flowable through the nozzle of the printing head of the bioprinter, as a lubricant could do.

The coagulation factor, such as thrombin, that can be added at any step of the manufacturing process of the hemostatic product, is used to promote coagulation. When different hemostatic flowable are used to print the different layers of the 3D-hemostatic product, an hemostatic flowable containing the coagulation factor can be printed in target zones only, for instance in zones where coagulation is required.

A 3D hemostatic product made with the proposed 3D printing process can be used quickly after having been manufactured with the 3D printer, e.g. within a few minutes. Since the fabrication process by a bioprinter is convenient and automatized, the 3D hemostatic product can be printed for immediate use following predesigned templates for instance, depending on a wound or bleeding site to heal.

Advantageously, the hemostatic product can be dried and applied dried on a bleeding site. If it is desired to use the 3D hemostatic product at a later stage, e.g. well after this above optimal usage recommendation, the 3D hemostatic product could be partially dried, at ambient atmosphere and/or in an autoclave for instance. In this case, the hemostatic product can be rehydrated before application on the wound. It is preferable to rehydrate the 3D hemostatic product before use, even though it is not absolutely necessary as it could be rehydrated with the blood surrounding the area where it has to be used.

The printed 3D-hemostatic product can be dried at room temperature or lyophilized, in order to better preserve collagen triple helical structure.

As indicated above, the proposed hemostatic flowable has the advantage of not requiring any cross-linking before or during the additive printing process to form cohesive stacked layers. It can however be considered having a cross-linking during the printing process to more finely control the joining of the layers and possibly perform more complex printing pattern. Such cross-linking could be for instance done by using a focused UV irradiation or any adapted chemical cross-linking process.

Moreover, the printed 3D hemostatic object can be cross-linked before or after being dried. The cross-linking can be local, in order to create a reinforced local zone, or in order to fix the printed shape locally. This is particularly advantageous to make a product with high resistance to manipulations and a higher bleeding flow strength. It has however to be noted that such cross-linking step is absolutely not necessary for the printing process to lead to cohesive, self-supporting, and resistant printed 3D products.

Alternatively, the cross-linking can concern the whole hemostatic product, in order to reinforce the hemostatic product, and particularly to impede or limit its swelling and deformation.

Local or general cross-linking can be induced by heat, light, or any suitable process.

As explained above, in case a specific cross-linking is required, it is preferable to have a cross-linking initiator within the composition on the hemostatic flowable used for printing the hemostatic product.

If the hemostatic product is devoid of coagulation factor, it could be soaked, dipped, sprayed with a coagulation factor, such as a thrombin solution, before or after drying. Alternatively, the coagulation factor can be absorbed or deposited on the product.

The components of the hemostatic flowable can be used sterile, but not necessarily. In this case, the printed hemostatic product can be sterilized before use.

A dried sterile printed hemostatic product can be applied on a bleeding wound.

Alternatively, the dried sterile printed hemostatic product can be soaked in a saline solution or/and a coagulation factor solution prior to its application on the bleeding wound.

The properties and corresponding use of the printed hemostatic product will depend on the properties of each of the layers forming this printed hemostatic product.

For instance, the composition and structure of the printed hemostatic product could be chosen to swell and deform in order to conform to the bleeding wound.

A possible pattern rich in coagulation factor can locally promote blood coagulation.

A possible "pro-adhesive" pattern can locally promote the product cohesion to or adhesion with the bleeding wound.

A possible external layer rich in water can advantageously prevent the product adhesion to surrounding tissues.

Using a printed hemostatic product formed with an hemostatic flowable as described above has the advantage of enhancing the contact surface with the wound. In particular, the contact with the bleeding area goes deeper. This is in particular of interest when the bleeding area corresponds to soft tissues and parenchymal organs.

The 3D hemostatic product being manufactured with a 3D additive printer, it can have any kind of three-dimensional structure, from a simple one being a full volume to a very complex one with a lot of lattices and angles.

The 3D hemostatic product can for instance have the shape of a rod, an hollow cylinder, a ball, etc. The 3D hemostatic product could also be a patch provided with a honeycomb structure, for instance a patch having the shape of a membrane with a thickness of at least a few millimeters (e.g. from 5 mm to 50 mm).

Advantageously, the hemostatic product can resorb, for instance a few weeks to several months after having been applied, according to size, thickness or possible cross-linking of the product.

As described above, we also propose a hemostatic method comprising the depositing of the printed hemostatic product such as defined above on a hemorrhaging part of an animal's body, including humans. In particular, the printed hemostatic product can be used in surgical procedures, in particular laparotomies, laparoscopies, coelioscopies and robotic procedures.

The printed hemostatic product described above could also be used as a cicatrizing agent for internal and external wounds. The expression "cicatrizing agent" refers to a product that makes it possible to obtain a clinically satisfactory healing of the tissues with which it is in contact.

EXAMPLES

Example 1

Protocol for Measuring Hemostatic Capacity in Vitro

Citrated (around 0.1 M) human blood is maintained at 37° C. in a water bath throughout the measurement. The product to be tested (10 mg) is deposited in a 5 mL polypropylene tube with a snap-on cap, and then citrated fresh blood (2 mL) is added. $CaCl_2$ is then added so that the final $CaCl_2$ concentration in the blood is 15 mM, and then the test tube is closed. The contents are then around mixed by vigorous inversions (10 times) and then the test tube is plunged into the water bath; the test tube is returned to the vertical position every 10 seconds. The time required to form a clot is noted and corresponds to hemostatic capacity.

Example 2

Protocol for Measuring Particle Size

A known quantity of product, notably of powder, is sifted through 50 μm, 100 μm, 200 μm, 300 μm and 400 μm screens for 2 minutes (per screen). The fractions from each screen are weighed. The proportion of each particle size range is determined.

Example 3

Protocol for Measuring the Swelling of the Composition

A 15 mL flask is weighed ($m_0$ in mg) and then X mg of powder of the dry composition is added ($m_{0+X}$ in mg). A 0.15 M aqueous NaCl solution (2 mL) is added and the composition is left to swell for 20 minutes; the flask is then centrifuged at 1,000 rpm.

Excess NaCl is removed with a Pasteur pipette and droplets are eliminated by turning over the flask on filter paper; the flask is then weighed with the wet powder ($m_1$ in mg).

The swelling ratio is calculated as follows: $((m_1-m_0)/(m_{0+x}-m_0))$.

Example 4

Preparation of Collagen of the Fibrillar Type by Basic Extraction

Pieces of pig dermis (30 kg), defatted with acetone, are left to swell for 3 hours in 100 kg of 0.05 M NaOH solution. The dermises are finely cut up by a cutting mill and the paste obtained is diluted with 50 liters of 0.05 M NaOH. The mixture is then sieved under pressure through a 1 mm screen. The paste obtained is then brought to pH 6-7.5 with HCl and the precipitate obtained is collected by centrifugation or filtration through a 1 mm screen.

The retentate is dehydrated with acetone according to methods known to those persons skilled in the art. This dehydrated retentate thus consists in collagen of the fibrillar type, with a large content of fibrillar/fibrous collagen relative to the non-fibrillar collagen. Generally, such extracted collagen comprises from 85% to 95% by weight of fibrillar/fibrous collagen relative to the total weight of the collagen, and from 5% to 15% by weight of non-fibrillar collagen relative to the total weight of the collagen.

Example 5

Preparation of a Hemostatic Powder #1

30 g of collagen of the fibrillar type as prepared in Example 4 is added to 1 L of a 0.02 M aqueous HCl solution and the mixture is then stirred for 5 hours. Next, to the homogeneous paste obtained, powdered fructose is added in an amount of 2% (0.6 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 μm.

Dermatan sulfate is then added to the powder in an amount of 2% by weight relative to the dry matter of the powder (0.612 g).

The mixture is then homogenized using a ball mill, lyophilized thrombin is added to the mixture in an amount of 15 IU/mg of powder, and finally the mixture is homogenized using a ball mill.

Example 6

Preparation of a Hemostatic Powder #2

7.5 kg of collagen of the fibrillar type as prepared in Example 4 is added to 50 L of a 0.05 M aqueous HCl solution and the mixture is then stirred for 16 hours. Next, to the homogeneous paste obtained, powdered fructose is added in an amount of 5% (375 g) by weight relative to the weight of the collagen.

The mixture is homogenized for 3 hours and then distributed onto plates and dehydrated. After drying, the dry product is ground by fraction at a rate of 5 g/min using a hammer mill at 12,000 rpm under controlled heating. The product is then screened by mechanical sifting to eliminate particles whose size is larger than 400 µm and those smaller than 50 µm.

Granulometry is measured in order to verify that the distribution is such that 60% of the sample by weight has a granulometry greater than 200 µm.

Purified chondroitin sulfates are then added to the powder in an amount of 20% by weight relative to the dry matter of the powder (1.575 kg). The mixture is homogenized using a ball mill.

Finally, lyophilized thrombin is added to the mixture in an amount of 10 IU/mg of powder. As before, the mixture is homogenized using a ball mill.

Example 7

Preparation of a Hemostatic Powder #3

1000 g of collagen of the fibrillar type as prepared in Example 4 is added to 60 mL of a 0.02 M aqueous HCl solution and the mixture is then stirred for 5 hours. Next, to the homogeneous paste obtained, powdered glucose is added in an amount of 5% (50 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm and smaller than 50 µm.

Chondroitin sulfate is then added to the powder in an amount of 10% by weight relative to the dry matter of the powder (105 g). The mixture is then homogenized using a ball mill.

Such powder composition has a tapped density of around 0.408 g/mL.

Example 8

Preparation of Hemostatic Powder #4

500 g of collagen of the fibrillar type as prepared in Example 4 is added to 30 mL of a 0.02 M aqueous HCl solution and the mixture is then stirred for 5 hours. Next, to the homogeneous paste obtained, powdered glucose is added in an amount of 5% (25 g) by weight relative to the weight of the collagen.

The mixture is homogenized for 1 hour and then poured out and dehydrated. After drying, the dry product is ground at a rate of 25 g/min using a Fitzpatrick hammer mill at 7,000 rpm under controlled heating. The product is then screened by mechanical sifting to eliminate particles whose size is larger than 400 µm and smaller than 50 µm.

Chondroitin sulfate mixed with a thrombin powder is then added to the powder in an amount of 10% by weight relative to the dry matter of the powder (52.5 g). The thrombin is added to the mixture in a final amount of 0.85 U/mg. The mixture is then homogenized using a ball mill.

Such powder composition has a tapped density of around 0.425 g/mL.

Example 9

Preparation of a Hemostatic Powder #5

750 g of collagen of the fibrillar type as prepared in Example 4 is mixed with 6675 mL of highly purified water. The mixture is stirred at a first stirring rate of 20 rpm during 10 minutes, and then at a second stirring rate of 40 rpm during 15 minutes.

The above mixture is then stirred again at the first stirring rate of 20 rpm while a solution of glucose (37.5 g of glucose with 300 mL of water) is incorporated. The quantity of glucose added corresponds to 5% by weight relative to the weight of the collagen being used in the mixture. This new mixture is stirred at the second stirring rate of 40 rpm during 10 minutes. This preparation is then stored during 16 hours.

A quantity of 87.5 mL of a 1 M aqueous HCl solution is then added to the preparation while being stirred at a stirring rate of 30 rpm. This new mixture is then stirred at a first stirring rate of 35 rpm during 1 minute, then at a second stirring rate of 40 rpm during 1 minute, followed then by several stirring sessions of 5 minutes at the same stirring rate of 40 rpm, a quick pause in the stirring being made between two sessions.

The thick paste obtained in the preceding phase is then separated in several pieces having similar shape and mass. Those pieces of the paste are then placed for 24 hours in a hermetically sealed enclosure having an atmosphere saturated with ammonia. After this neutralization step, the pieces of paste are dried at 20° C. during 96 hours, and the dry products are then ground at a rate of 1 kg/h using a cryogenic mill of Forplex at 8,500 rpm. The powder product is then screened by mechanical sifting to eliminate particles whose size is larger than 200 µm and smaller than 50 µm, resulting in a collagen-glucose powder.

A powder of chondroitin sulfate (CS) which is made of particles having a size between 50 µm and 200 µm is then added to the collagen-glucose powder in an amount of 10% by weight relative to the dry matter of the collagen-glucose powder. For instance, 30 g of the powder of chondroitin sulfate is mixed with 300 g of the collagen-glucose powder. For this hemostatic powder #5, freeze-dried thrombin is also added, in a quantity of 1000 UI/g. The mixture is then homogenized using a V blender. The final hemostatic powder has a tapped density of around 0.4 g/mL.

Example 10

Collagen Characterization→Presence of Soluble Collagen in the Collagen, Determination of the Ratio Between Fibrillar/Fibrous Collagen and Non-Fibrillar Collagen The goal of the experimentation is to determine the proportion of fibrillar/fibrous collagen and non-fibrillar collagen in a collagen (extracted collagen or collagen ground into powder). Such proportion can be determined by studying the proportion of insoluble (corresponding to the fibrillar/fibrous collagen) and soluble collagen (corresponding to the non-fibrillar collagen) in the collagen.

The experimentation consists in solubilizing about 2.5 g of the collagen under test in 166 mL of water at pH 13 during 16 hours. The solution is then centrifuged (10000 rpm during 10 minutes). The supernatant (corresponding to the non-fibrillar collagen) and the residue (corresponding to the fibrous/fibrillar collagen) are then split. The residue is directly dried with successive acetone baths and under a controlled air flow. The pH of the supernatant is adjusted at pH 3 with acetic acid and chlorhydric acid at 6M. The solid collagen from the supernatant is obtained by adding NaCl 0.6M, and by performing a centrifugation. It is then dried with successive acetone baths and under a controlled air flow.

The collagen weights from the residue (Mresidue) and from the supernatant (Msupernatant) are calculated, and the formula Mresidue/(Mresidues+Msupernatant)×100 gives the percentage of fibrous collagen on total amount of collagen.

In the invention, the ratio Mresidue/(MResidues+Msupernatant) must be superior to 80% both for the collagen used to prepare the powder and for the final collagen powder. Preferentially the ratio is superior to 85%.

For example, the above experimentation made of three batches of collagen prepared as in example 4 gives very similar ratios of 92.67%, 94.60% and 91.51% respectively. After having ground the collagen of these three batches, the ratio remains very similar as it is of 91.63%, 88.02%, and 88.69% respectively.

Another way to show the presence of both fibrous/fibrillar collagen and soluble collagen is to perform a SDS page electrophoresis.

Figure 2:
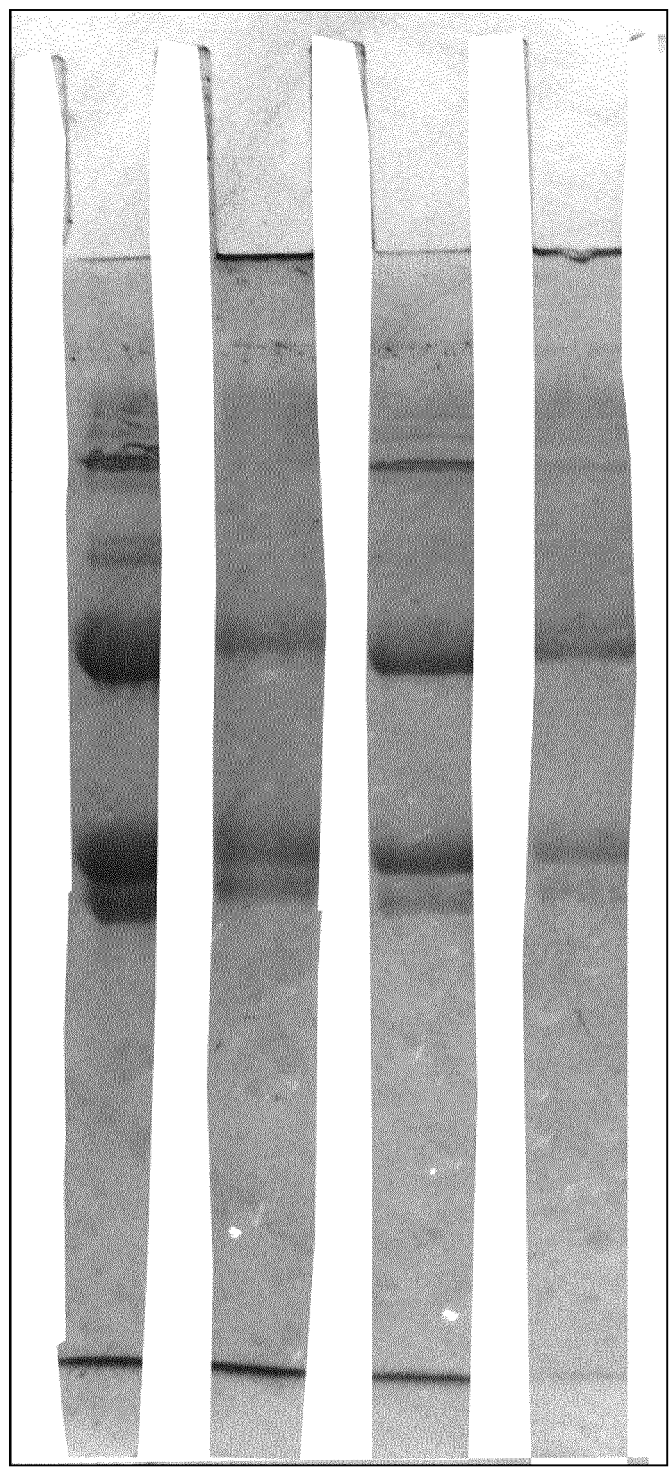
FIG. 2 is an example of a result of an electrophoresis as described in example 10.

FIG. 2 illustrates such electrophoresis, with sample 51 corresponding to the supernatant of a first batch (made from collagen extracted as in example 4), sample S2 corresponding to the residue of this first batch, and sample S3 corresponding to the supernatant of a second batch (also made from collagen extracted as in example 4), sample S4 corresponding to the residue of this second batch.

The results show that for the collagen from the residue, a larger amount of fiber cannot migrate through the acrylamide gel and are stained at the stop of the gel. The preparation of the sample does not allow the split of each chain from the collagen. Therefore, alpha chains are present in a very low amount. The collagen from the supernatant is able to entirely migrate in the gel, there are no fiber blocked at the top, chains from the collagen are properly split during the electrophoresis process.

Bibliographic Data
WO 2012/146655
"Nature designs tough collagen: explaining the nanostructure of collagen fibrils," by Markus Buehler (PNAS, Aug. 15, 2006, vol.103, no. 33, pp. 12285-12290)
"Extraction of collagen from connective tissue by neutral salt solutions" by Jerome Gross, John H. Highberger and Francis O. Schmitt (Proceedings of the NATIONAL ACADEMY OF SCIENCES Volume 41 Number I Jan. 15, 1955)
WO 2010/125086
FR2944706
WO 01/97873
U.S. Pat. No. 4,891,359
"Current advances and future perspectives in extrusion-based bioprinting" by Ibrahim T. Ozbolat and Monika Hospodiuk (Biomaterials 76 (2016) 321-343)
"Biomimetic 4D printing" by A. Sydney Gladman et al. entitled (Nature Materials volume 15, pages 413-418 (2016))

The invention claimed is:

1. A printed hemostatic product having three-dimensions and being made of a stack of layers deposited on one another from a first external layer up to a second external layer, wherein a plurality of adjacent layers of the stack of layers are joined together, and wherein each of the plurality of adjacent layers of the stack of layers has at least one portion made from an hemostatic flowable with a composition comprising:
   non-cross-linked collagen of the fibrillar type comprising a content of fibrous collagen and/or fibrillar collagen of at least 70% by weight relative to the total weight of the collagen; and
   at least one monosaccharide
   wherein at least one layer of the plurality of adjacent layers of the stack of layers has several portions made from hemostatic flowables with different compositions.

2. The printed hemostatic product of claim 1, wherein at least one layer of the plurality of adjacent layers of the stack of layers is fully made from the same hemostatic flowable.

3. The printed hemostatic product of claim 1, wherein at least one of the first and second external layers of the stack of layers has a portion made from the hemostatic flowable.

4. The printed hemostatic product of claim 3, wherein the at least one of the first and second external layers is fully made from the same hemostatic flowable.

5. The printed hemostatic product of claim 1, wherein at least one layer of the stack of layers comprises a portion made from an hemostatic flowable having swelling properties different from the swelling properties of the other layers of the stack of layers.

6. The printed hemostatic product of claim 1, wherein the hemostatic flowable is made with an hemostatic powder having a composition comprising:
   collagen of the fibrillar type comprising a content of fibrous collagen and/or fibrillar collagen of at least 70% by weight relative to the total weight of the collagen, said collagen being in an amount ranging from 75% to 96% by weight relative to the total weight of the composition of the hemostatic powder, and
   least one monosaccharide in an amount ranging from 1% to 12.5% by weight relative to the total weight of the composition of the hemostatic powder.

7. A method of producing a printed hemostatic product of claim 1, with an hemostatic flowable as a printing ink for a three-dimensional printer, wherein the hemostatic flowable is made of a hemostatic powder mixed with a saline solution, wherein the hemostatic powder has a composition comprising:
   non-cross-linked collagen of the fibrillar type comprising a content of fibrous collagen and/or fibrillar collagen of at least 70% by weight relative to the total weight of the collagen; and
   at least one monosaccharide.

8. The method of claim 7, wherein the composition of the hemostatic powder forming the hemostatic flowable comprises:
   collagen of the fibrillar type comprising a content of fibrous collagen and/or fibrillar collagen of at least 70% by weight relative to the total weight of the collagen, said collagen being in an amount ranging from 75% to 96% by weight relative to the total weight of the composition of the hemostatic powder; and east one monosaccharide in an amount ranging from 1% to 12.5% by weight relative to the total weight of the composition of the hemostatic powder.

9. Method of manufacturing an hemostatic product of claim 1 having three dimensions with a three-dimensional additive printer, comprising the following steps:
a) providing a three-dimensional model to the three-dimensional additive printer, said three-dimensional model corresponding to the structure of the hemostatic product to be manufactured, and processing said three-dimensional model to define a printing pattern with a plurality of layers designed to be stacked on one another so as to form a stack of layers corresponding to the three-dimensional model;
b) providing at least one hemostatic flowable to the three-dimensional additive printer for use as a printing ink, wherein said flowable is made of an hemostatic powder mixed with a saline solution, wherein the hemostatic powder has a composition comprising:
non-cross-linked collagen of the fibrillar type comprising a content of fibrous collagen and/or fibrillar collagen of at least 70% by weight relative to the total weight of the collagen; and
at least one monosaccharide;
c) printing the hemostatic product with the three-dimensional additive printer by depositing printing ink to successively print layers on one another, said forming comprising depositing the hemostatic flowable with the three-dimensional additive printer to form at least one portion of at least one layer of the stack of layers.

10. The method of claim 9, wherein at least one layer of the stack of layers is entirely made with the deposition of the hemostatic flowable.

11. The method of claim 9, wherein in step b), a plurality of hemostatic flowables are provided to the three-dimensional additive printer for use as printing inks, said hemostatic flowables having different compositions.

12. The method of claim 9, wherein the composition of the hemostatic powder forming the hemostatic flowable comprises:
collagen of the fibrillar type comprising a content of fibrous collagen and/or fibrillar collagen of at least 70% by weight relative to the total weight of the collagen, said collagen being in an amount ranging from 75% to 96% by weight relative to the total weight of the composition of the hemostatic powder; and
least one monosaccharide in an amount ranging from 1% to 12.5% by weight relative to the total weight of the composition of the hemostatic powder.

13. The method of claim 9, wherein the printing step c) is done at ambient atmosphere.

14. The method of claim 9, wherein after the hemostatic product has been formed in the printing step c), a coating step d) is performed wherein a solution including a coagulation factor is used to coat an external surface of the hemostatic product.

15. The method of claim 14, wherein the coating step d) is performed by spraying the solution including a coagulation factor on the external surface of the hemostatic product.

16. The method of claim 9, wherein after the hemostatic product has been formed in the printing step c), a soaking step e) is performed wherein the hemostatic product is soaked in a solution including a coagulation factor.

17. The method of claim 9, wherein the final step of manufacturing the hemostatic product consists in maintaining the printed hemostatic product in ambient atmosphere for a predetermined resting period.

18. The method of claim 9, wherein the whole process is performed at ambient atmosphere without any photo-stimulation or heat stimulation of the hemostatic product.

19. A printed hemostatic product having three-dimensions and being made of a stack of layers deposited on one another from a first external layer up to a second external layer, wherein a plurality of adjacent layers of the stack of layers are joined together, and wherein each of the plurality of adjacent layers of the stack of layers has at least one portion made from an hemostatic flowable with a composition comprising:
non-cross-linked collagen of the fibrillar type comprising a content of fibrous collagen and/or fibrillar collagen of at least 70% by weight relative to the total weight of the collagen; and
at least one monosaccharide;
wherein all layers of the stack of layers have the same composition.

20. A printed hemostatic product having three-dimensions and being made of a stack of layers deposited on one another from a first external layer up to a second external layer, wherein a plurality of adjacent layers of the stack of layers are joined together, and wherein each of the plurality of adjacent layers of the stack of layers has at least one portion made from an hemostatic flowable with a composition comprising:
non-cross-linked collagen of the fibrillar type comprising a content of fibrous collagen and/or fibrillar collagen of at least 70% by weight relative to the total weight of the collagen; and
at least one monosaccharide;
wherein the first and second external layers of the stack of layers are made from an hemostatic flowable of the same composition, and wherein each layer of the stack of layers has a peripheral portion made from a flowable mixture identical to the flowable mixture of the first and second external layers.

* * * * *